(12) United States Patent
Garcia-Blanco et al.

(10) Patent No.: US 10,961,581 B2
(45) Date of Patent: Mar. 30, 2021

(54) METHOD TO IDENTIFY SUBJECTS AT HIGHER RISK TO DEVELOP AN AUTOIMMUNE DISEASE BASED ON GENETIC AND/OR PHENOTYPIC SCREENING FOR EPISTATIC VARIANTS IN DDX39B (RS2523506) AND IL7R (RS6897932)

(71) Applicant: BOARD OF REGENTS, THE UNIVERSITY OF TEXAS SYSTEM, Austin, TX (US)

(72) Inventors: Mariano A. Garcia-Blanco, Galveston, TX (US); Gaddiel Galarza-Munoz, Galveston, TX (US); Simon G. Gregory, Durham, NC (US); Farren B. S. Briggs, Cleveland Heights, OH (US); Lisa F. Barcellos, El Cerrito, CA (US); Shelton S. Bradrick, Galveston, TX (US); Irina Evsyukova, Cedar Grove, NC (US); Dennis C. Ko, Durham, NC (US)

(73) Assignees: Board of Regents, The University of Texas System, Austin, TX (US); Duke University, Durham, NC (US); Case Western Reserve, Cleveland, OH (US); The Regents of the University of California, Oakland, CA (US)

(*) Notice: Subject to any disclaimer, the term of this patent is extended or adjusted under 35 U.S.C. 154(b) by 199 days.

(21) Appl. No.: 15/928,939

(22) Filed: Mar. 22, 2018

(65) Prior Publication Data
US 2018/0274033 A1 Sep. 27, 2018

Related U.S. Application Data

(60) Provisional application No. 62/474,951, filed on Mar. 22, 2017.

(51) Int. Cl.
| | | |
|---|---|---|
| C12Q 1/68 | (2018.01) | |
| C12Q 1/6883 | (2018.01) | |
| C12Q 1/34 | (2006.01) | |
| C12Q 1/6806 | (2018.01) | |
| C12Q 1/6851 | (2018.01) | |
| C12Q 1/683 | (2018.01) | |
| C12Q 1/686 | (2018.01) | |

(52) U.S. Cl.
CPC .......... *C12Q 1/6883* (2013.01); *C12Q 1/34* (2013.01); *C12Q 1/6806* (2013.01); *C12Q 1/683* (2013.01); *C12Q 1/686* (2013.01); *C12Q 1/6851* (2013.01); *C12Q 2600/156* (2013.01); *C12Y 306/04013* (2013.01)

(58) Field of Classification Search
None
See application file for complete search history.

(56) References Cited

U.S. PATENT DOCUMENTS

2015/0152474 A1* 6/2015 Pawlowski .......... C12Q 1/6886
506/4

OTHER PUBLICATIONS

Allcock, et al., "The Central MHC Gene, BAT1, May Encode a Protein that Down-Regulates Cytokine Production", Blackwell Science Limited, Genes to Cells, 2001, 6, 487-494.
Alves, et al., "Differential Regulation of Human IL-7 Receptor Expression by IL-7 and TCR Signaling1" The American Association of Immunologists, Inc., 2008, 0022-1767.
Anderson et al., "Meta-analysis identifies 29 Additional Ulcerative Colitis Risk Loci, Increasing the Number of Confirmed Associations to 47", Nature Genetics, Mar. 2011, vol. 43, No. 3.
Badot et al., "Rheumatoid Arthritis Synovial Fibroblasts Produce a Soluble Form of the Interleukin-7 Receptor in Response to Pro-Inflammatory Cytokines", Journal of Cellular and Molecular Medicne, doi:10.1111/i.1582-4934.2010.01228.x.
Barrett et al. "Genome-wide association study and meta-analysis find that over 40 loci affect risk of type 1 diabetes", Nature Genetics vol. 41, No. 6, Jun. 2009.
Bilal et al., "Optimization of methods for the genetic modification of human T cells", Immunology and Cell Biology (2015) 93, 896-908.
Briggs et al., Supervised machine learning and logistic regression identifies novel epistatic risk factors with PTPN22 for rheumatoid arthritis, Genes and Immunity (2010) 11, 199-208.
Browning et al., "A Unified Approach to Genotype Imputation and Haplotype-Phase Inference for Large Data Sets of Trios and Unrelated Individuals", The American Journal of Human Genetics 84, 210-223, Feb. 13, 2009.
Cheong et al., "Localization of Central MHC Genes Influencing Type I Diabetes", Human Immunology 62, 1363-1370 (2001).

(Continued)

*Primary Examiner* — Stephanie K Mummert
(74) *Attorney, Agent, or Firm* — Chalker Flores, LLP; Edwin S. Flores

(57) ABSTRACT

The present invention includes a method, kits, and assays for identifying a human subject as having an increased risk of developing an autoimmune disease, or a human subject with multiple sclerosis caused by elevated soluble Interleukin 7 receptor (sIL7R), by obtaining a biological sample and detecting or measuring in the biological sample an amount of a soluble Interleukin-7 receptor (sIL7R) and an amount of an RNA Helicase DDX39B, whereby a lower expression of DDX39B and a higher secretion of sIL7R identifies the subject from which the biological sample was obtained as having an increased risk of developing an autoimmune disease, when compared to a human subject not having an autoimmune disease. The present invention also includes a method of modifying a treating of subjects based on the lower expression of RNA Helicase DDX39B alone or in combination with an increase in sIL7R.

2 Claims, 7 Drawing Sheets

Specification includes a Sequence Listing.

(56) References Cited

OTHER PUBLICATIONS

Crawley et al., "Soluble IL-7Ra (sCD127) Inhibits IL-7 Activity and Is Increased in HIV Infection", Copyright, 2010 by The American Association of Immunologists, Inc. 0022-1767/10.

W. de Bakker et al., "A high-resolution HLA and SNP haplotype map for disease association studies in the extended human MHC", Nature Genetics, vol. 38, No. 10, Oct. 2006.

Degli-Esposti et al., "Ancestral Haplotypes Carry Haplotypic and Haplospecific Polymorphisms of BAT1: Possible Relevance to Autoimmune Disease", European Journal of Immunogenetics (1992), 19, 121-127.

Dooms, "Interleukin-7: Fuel for the autoimmune attack", Journal of Autoimmunity 45 (2013) 40-48.

Evsyukova et al., "Cleavage and polyadenylation specificity factor 1 (CPSF1) regulates alternative splicing of interleukin 7 receptor (IL7R) exon 6", RNA (2013), 19:00-00. Published by Cold Spring Harbor Laboratory Press. Copyright, 2013 RNA Society, Downloaded from rnajournal.cshlp.org on Jul. 6, 2018.

Fleckner et al., "U2AF 65 recruits a novel human DEAD box protein required for the U2 snRNP-branchpoint interaction", Genes & Development 11:1864-1872, 1997 by Cold Spring Harbor Laboratory Press ISSN 0890-9369/97.

Fry et al., "The Many Faces of IL-7: From Lymphopoiesis to Peripheral T Cell Maintenance", Copyright © 2005 by The American Association of Immunologists, Inc., 0022-1767/05.

Gregory et al., "Interleukin 7 receptor a chain (IL7R) shows allelic and functional association with multiple sclerosis", Nature Genetics, vol. 39—No. 9—Sep. 2007.

Hafler at al., "Risk Alleles for Multiple Sclerosis Identified by a Genomewide Study", The New England Journal of medicine, Aug. 30, 2007, vol. 357, No. 9.

Hoe et al, "Functionally Significant Differences in Expression of Disease-Associated IL-7 Receptor a Haplotypes in CD4 T Cells and Dendritic Cells", The Jouurnal of Immunology, 0022-1767/2010.

Honig et al., "Regulation of Alternative Splicing by the ATP-Dependent DEAD-Box RNA Helicase p72", Molecular and Cellular Biology, Aug. 2002, p. 5698-5707.

Huang et al., "DDX5 and its associated lncRNA Rmrp modulate Th17 cell effector functions", Dec. 24-31, 2015, vol. 528, Nature, 517.

The International HapMap Consortium, Nature, vol. 426, 18/25m Dec. 2003.

The International HapMap Consortium, "A haplotype map of the human genome", Nature. Oct. 27, 2005; 437 (7063): 1299-1320.

The International HapMap Consortium, "A second generation human haplotype map of over 3.1 million SNPs", Nature 06258, vol. 449, Oct. 8, 2007, doi:10.1038.

The International HIV Controllers Study, "The Major Genetic Determinants of HIV-1 Control Affect HLA Class I Peptide Presentation", Science, Dec. 10, 2010; 330(6010): 1551-1557.

Irimia et al., "A Highly Conserved Program of Neuronal Microexons Is Misregulated in Autistic Brains", Cell 159, 1511-1523, Dec. 18, 2014, 2014 Elsevier Inc.

Kaiser et al., "Activation of cap-independent translation by variant eukaryotic initiation factor 4G in vivo", RNA (2008), 14:1-13.

Kilding et al., "Additional Genetic Susceptibility for Rheumatoid Arthritis Telomeric of the DRB1 Locus", Arthritis & Rheumatism, vol. 50, No. 3, Mar. 2004, pp. 763-769.

Lauwerys et al., "sIL7R concentrations in the serum reflect disease activity in the lupus kidney", Lupus Science and Medicine, 2014;1:e000036. doi:10.1136.

Lawson et al., "Interleukin-7 is required for CD4+ T cell activation and autoimmune neuroinflammation", Clinical Immunology 161 (2015) 260-269.

Lundmark et al., "Variation in interleukin 7 receptor a chain (IL7R) influences risk of multiple sclerosis", Nature Genetics, Jul. 29, 2007; doi:10.1038/ng2106.

Lundstrom et al., "Soluble IL7Rα potentiates IL-7 bioactivity and promotes autoimmunity", PNAS Early Edition, 1 of 10, www.pnas.org/cgi/doi/10.1073/pnas.1222303110.

Luo et al., "Pre-mRNA splicing and mRNA export linked by direct interactions between UAP56 and Aly", Letters to Nature, vol. 413, Oct. 11, 2001.

Maraskovsky et al., "Impaired survival and proliferation in IL-7 receptor-deficient peripheral T cells", The Journal of Immunology, 1996; 157:5315-5323.

Masuda et al., "Recruitment of the human TREX complex to mRNA during splicing", Genes and Development, 19:1512-1517. 2005.

Mazzucchelli et al., "Interleukin-7 receptor expression: intelligent design", Nature Publishing group, vol. 7, Feb. 2007.

Monti et al., "Concentration and activity of the soluble form of the Interleukin-7 Receptor alpha in type I diabetes identifies an interplay between hyperglycemia and immune function", Diabetes Publish Ahead of Print, published online Mar. 1, 2013.

Moutsianas et al., "Class II HLA interactions modulate genetic risk for multiple sclerosis", Nature Genetics, vol. 47, No. 10, Oct. 2015.

Munitic et al., "Dynamic regulation of IL-7 receptor expression is required for normal thymopoiesis", Immunobiology, Blood, Dec. 15, 2004, vol. 104, No. 13.

Nakamura et al., "Genome-wide Association Study Identifies TNFSF15 and POU2AF1 as Susceptibility Loci for Primary Biliary Cirrhosis in the Japanese Population", The American Journal of Human Genetics, 91, 721-728, Oct. 5, 2012.

Okamoto et al., "Identification of IkBL as the Second Major Histocompatibility Complex-Linked Susceptibility Locus for Rheumatoid Arthritis", Am. J. Hum. Genet. 72:303-312, 2003.

Park et al., "Suppression of IL7R Transcription by IL-7 and Other Prosurvival Cytokines: a Novel Mechanism for Maximizing IL-7-Dependent T Cell Survival", Immunity, vol. 21, 289-302, Aug. 2004.

Paternoster et al., "Meta-analysis of genome-wide association studies identifies three new risk loci for atopic dermatitis", Nature Genetics, vol. 44, No. 2, Feb. 2012.

IDS SB08-Part 1, 011519.

Transmittal IDS Part 1, 011519.

IDS SB08-Part 2, 011519.

Transmittal IDS Part 2, 011519.

Patsopoulos et al., "Genome-Wide Meta-Analysis Identifies Novel Multiple Sclerosis Susceptibility Loci", American Neurological Association, 2011, vol. 70, No. 6.

Patsopoulos et al., "Fine-Mapping the Genetic Association of the Major Histocompatibility Complex in Multiple Sclerosis: HLA and Non-HLA Effects", PLoS Genetics, Nov. 2013, vol. 9, Issue 11.

Perdigones et al., "Evidence of Epistasis Between TNFRSF14 and TNFRSF6B Polymorphisms in Patients With Rheumatoid Arthritis", Arthritis and Rheumatism, vol. 62, No. 3, Mar. 2010, pp. 705-710.

Peschon et al., "Early Lymphocyte Expansion Is Severely Impaired in Interleukin 7 Receptor-deficient Mice", J. Exp. Med., vol. 180, Nov. 1994, pp. 1955-1960.

Price et al., "Polymorphisms at positions −22 and −348 in the promoter of the BAT1 gene affect transcription and the binding of nuclear factors", Human Molecular Genetics, 2004, vol. 13, No. 9, pp. 967-974.

Puel, A. et al. "Defective IL7R expression in T(−)B(+)NK(+) severe combined immunodeficiency." Nature genetics (1998), 20:394-397.

Purcell, S., et al., "PLINK: a tool set for whole-genome association and population-based linkage analyses." American journal of human genetics (2007), 81:559-575.

Quinones-Lombrana, A., et al., "BAT1 promoter polymorphism is associated with rheumatoid arthritis susceptibility." J Rheumatol (2008), 35:741-744.

Raychaudhuri, S., et al., "Five amino acids in three HLA proteins explain most of the association between MHC and seropositive rheumatoid arthritis." Nature genetics (2012), 44:291-296.

Roifman, C.M., et al., "A partial deficiency of interleukin-7R alpha is sufficient to abrogate T-cell development and cause severe combined immunodeficiency." Blood (2000), 96:2803-2807.

Shahbazi, M., et al., "Interaction of HLA-DRB1*1501 allele and TNF-alpha −308 G/A single nucleotide polymorphism in the susceptibility to multiple sclerosis." Clin Immunol (2011), 139:277-281.

(56) References Cited

OTHER PUBLICATIONS

Shen, H., et al., "Distinct activities of the DExD/H-box splicing factor hUAP56 facilitate stepwise assembly of the spliceosome." Genes Dev (2008), 22:1796-1803.

Shen, J., et al., "Biochemical characterization of the ATPase and helicase activity of UAP56, an essential pre-mRNA splicing and mRNA export factor." J Biol Chem (2007), 282:22544-22550.

Sospedra, M., et al., "Immunology of multiple sclerosis." Annual review of immunology (2005), 23:683-747.

Strasser, K., et al., "TREX is a conserved complex coupling transcription with messenger RNA export." Nature (2002), 417:304-308.

Teigelkamp, S., et al., "The human U5 snRNP-specific 100-kD protein is an RS domain-containing, putative RNA helicase with significant homology to the yeast splicing factor Prp28p." RNA (1997), 3:1313-1326.

Todd J.A., et al., "Robust associations of four new chromosome regions from genome-wide analyses of type 1 diabetes." Nature genetics (2007), 39:857-864.

Wagner, E.J., et al., "RNAi-mediated PTB depletion leads to enhanced exon definition." Mol Cell (2002), 10:943-949.

Wong, A.M., et al., "Alleles of the proximal promoter of BAT1, a putative anti-inflammatory gene adjacent to the TNF cluster, reduce transcription on a disease-associated MHC haplotype." Genes Cells (2003), 8:403-412.

Wu, L., et al., "Variation and genetic control of protein abundance in humans." Nature (2013), 499:79-82.

Yuan, Y., et al., "Analysis of genome-wide RNA-sequencing data suggests age of the CEPH/Utah (CEU) lymphoblastoid cell lines systematically biases gene expression profiles." Sci Rep (2015), 5:7960.

Zhou X.J. et al., "Gene-gene interaction of BLK, TNFSF4, TRAF1, TNFAIP3, and REL in systemic lupus erythematosus." Arthritis and rheumatism (2012), 64:222-231.

\* cited by examiner

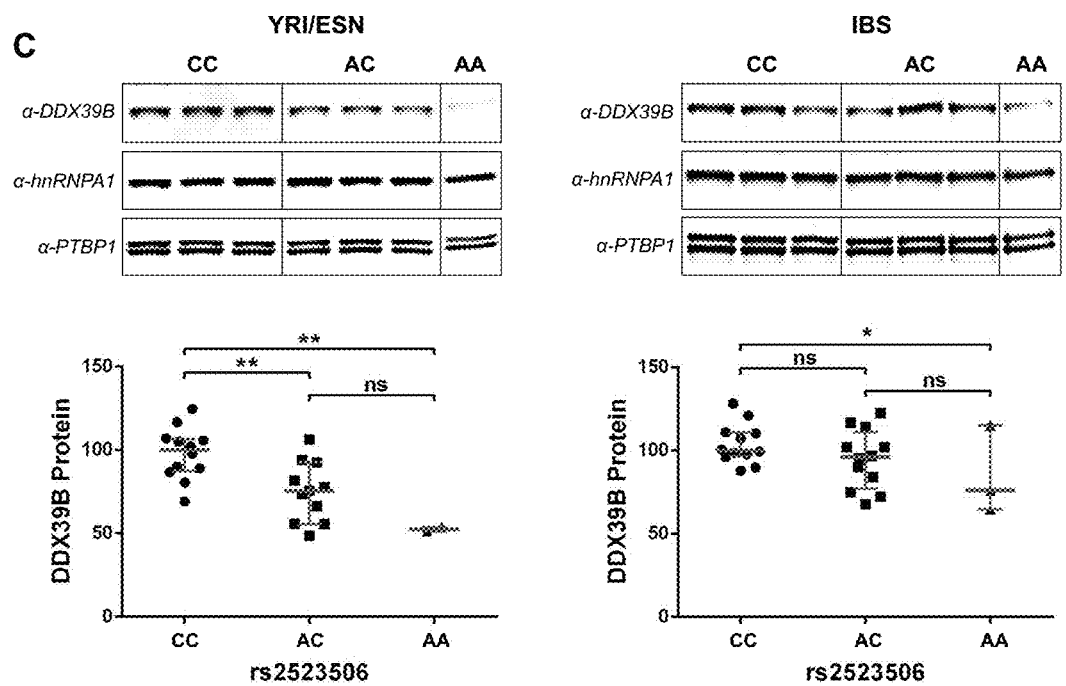
FIG. 3C
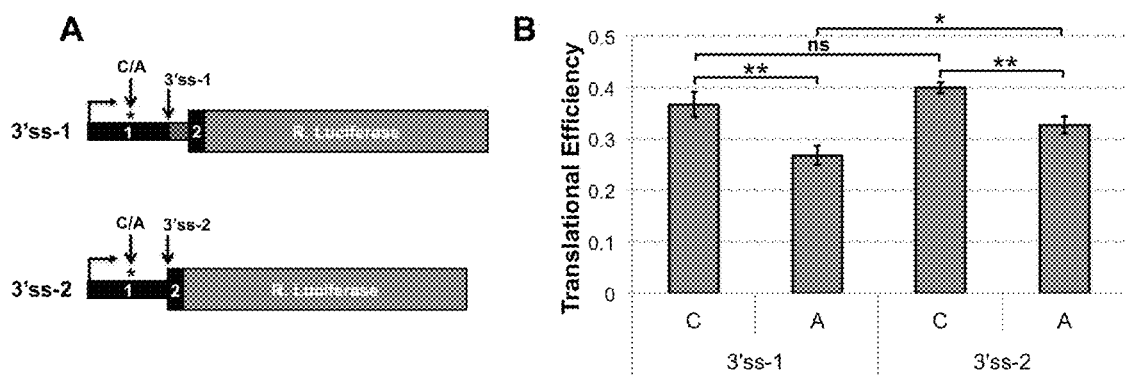
FIG. 4A
FIG. 4B

METHOD TO IDENTIFY SUBJECTS AT HIGHER RISK TO DEVELOP AN AUTOIMMUNE DISEASE BASED ON GENETIC AND/OR PHENOTYPIC SCREENING FOR EPISTATIC VARIANTS IN DDX39B (RS2523506) AND IL7R (RS6897932)

CROSS-REFERENCE TO RELATED APPLICATIONS

This application claims priority to U.S. Provisional Application Ser. No. 62/474,951, filed Mar. 22, 2017, the entire contents of which are incorporated herein by reference.

STATEMENT OF FEDERALLY FUNDED RESEARCH

This invention was made with government support under R01-NS060925, and F32-NS087899, awarded by NIH/NINDS. The government has certain rights in the invention.

TECHNICAL FIELD OF THE INVENTION

The present invention relates in general to the field of genetic or phenotypic testing for risk of autoimmune disorders, and more particularly, to a novel method for identifying subjects at risk for multiple sclerosis.

BACKGROUND OF THE INVENTION

Without limiting the scope of the invention, its background is described in connection with multiple sclerosis.

Multiple Sclerosis (MS) is a chronic autoimmune disorder characterized by self-reactive T cell-mediated damage to neuronal myelin sheaths in the central nervous system (CNS) that leads to axonal demyelination, neuronal death and progressive neurological dysfunction. Up to date, there is no cure for the disease and available treatments can only slow down disease progression, often by suppressing the immune system. Unfortunately, patients are normally diagnosed after manifestation of clinical symptoms, at which time the patient has suffered substantial neuronal damage and this cannot be reverted with current approved treatments. Therefore, there is an unmet need for early detection and diagnosis of MS.

The breach of immunological tolerance that leads to MS is thought to originate from complex interactions between environmental and genetic factors. Under this view, the genetic background of an individual could generate an environment permissive for the survival of self-reactive lymphocytes, which could be subsequently activated by the presence of an environmental trigger, usually in the form of viral or bacterial infection. Accordingly, methods for genetic screening of variants associated with increased MS risk could provide a valuable tool to identify individuals at higher risk to develop MS.

U.S. Pat. No. 8,158,344 shows that a driver of increased MS risk is the soluble form of the interleukin-7 receptor alpha chain gene (sIL7R), produced by alternative splicing of IL7R exon 6. The present inventors and others have previously shown that the variant rs6897932 (C/T, where C is the risk allele) within IL7R exon 6 is strongly associated with increased MS risk (Gregory et al., 2007; International Multiple Sclerosis Genetics et al., 2007; Lundmark et al., 2007). Furthermore, the present inventors showed that the risk 'C' allele of this variant increases skipping of the exon (Evsyukova et al., 2013; Gregory et al., 2007), leading to up-regulation of sIL7R (Hoe et al., 2010; Lundstrom et al., 2013). Importantly, sIL7R has been shown to exacerbate the clinical progression and severity of the disease in the Experimental Autoimmune Encephalomyelitis (EAE) mouse model of MS, presumably by potentiating the bioavailability and/or bioactivity of IL-7 cytokine (Lundstrom et al., 2013). Collectively, these data link alternative splicing of IL7R to the pathogenesis of MS, and U.S. Pat. No. 8,158,344 describes methods for screening based on the effects of IL7R rs6897932.

SUMMARY OF THE INVENTION

In one embodiment, the present invention includes a method of identifying a human subject as having an increased risk of developing an autoimmune disease caused by lower levels of an RNA Helicase DDX39B, comprising: obtaining a biological sample from a subject suspected of having an autoimmune disease; and detecting or measuring in the biological sample an amount of an RNA Helicase DDX39B, whereby a lower expression of DDX39B identifies the subject from which the biological sample was obtained as having an autoimmune disease or having increased risk of developing an autoimmune disease, when compared to a human subject not having an autoimmune disease. In one aspect, the method further comprises the step of measuring the expression levels of the soluble isoform of the Interleukin-7 Receptor (sIL7R), wherein a higher secretion of sIL7R and a lower expression of DDX39B identifies the subject from which the biological sample was obtained as having an autoimmune disease or having increased risk of developing an autoimmune disease, when compared to a human subject not having an autoimmune disease because DDX39B is a critical splicing factor required for inclusion of exon 6 in IL7R pre-mRNAs. In another aspect, the autoimmune disease is selected from Multiple sclerosis, Type I diabetes, Rheumatoid arthritis, Systemic lupus erythematosus, Atopic dermatitis, Ankylosing spondylitis, Primary biliary cirrhosis, or inflammatory bowel syndromes such as Ulcerative colitis and Crohn's disease. In another aspect, the step of detecting or measuring in the biological sample is defined further as being selected from at least one of: detecting a presence of the risk alleles at SNPs associated with multiple sclerosis in DDX39B and IL7R genes, at least one SNP selected from at least rs6897932 and rs2523506, or any allele in linkage disequilibrium with the DDX39B and IL7R MS risk alleles; a differential expression of IL7R RNA isoforms; a differential expression of IL7R protein isoforms; a differential expression of DDX39B protein; or any combination thereof; detecting or measuring in the biological sample is defined further as detecting allelic variants in DDX39B nucleic acids, which encodes an RNA helicase critical for inclusion of exon 6 in the Interleukin-7 receptor (IL7R) mRNA, whereby the presence of the risk A allele at the SNP rs2523506 in DDX39B exon 1 (5' UTR of DDX39B mRNAs), or the presence of the complementary allele in the opposite strand, or the presence of any other allele in linkage disequilibrium with rs2523506, identifies the subject from which the biological sample was obtained as having multiple sclerosis or having an increased risk of developing multiple sclerosis, relative to a biological sample from a human subject lacking the risk allele at the SNP rs2523506; detecting or measuring in the biological sample is defined further as detecting allelic variants in DDX39B and the Interleukin-7 receptor (IL7R), whereby the presence of the risk A allele at the SNP rs2523506 in DDX39B exon 1 (5' UTR of DDX39B mRNAs) and the presence of the risk C allele at the SNP rs6897932 in IL7R exon 6, or the presence of the complementary allele in the opposite strand, or the presence of any other allele in linkage disequilibrium with at least one of rs2523506 or rs6897932, identifies the subject from which the biological sample was obtained as having multiple sclerosis or an increased risk of developing multiple sclerosis, relative to a biological sample from a human subject lacking the risk allele at the SNPs rs2523506 and/or rs6897932; detecting or measuring in the biological sample is defined further as detecting phenotypic differences in the expression of Interleukin-7 receptor (IL7R) mRNA isoforms and RNA Helicase DDX39B, whereby an elevated fraction of IL7R mRNAs that lack exon 6 in the biological sample from an individual carrier of the risk alleles at rs6897932 and/or rs2523506, or any other variant in linkage disequilibrium with rs6897932 and/or rs2523506, identifies the subject from which the biological sample was obtained as having multiple sclerosis or an increased risk of developing multiple sclerosis, relative to a biological sample from a human subject lacking the risk allele at the SNPs rs2523506 and/or rs6897932; detecting or measuring in the biological sample is defined further as detecting phenotypic differences in the expression of Interleukin-7 receptor (IL7R) protein isoforms and RNA Helicase DDX39B, whereby elevated levels of the soluble form of IL7R (sIL7R) in the biological sample from an individual carrier of the risk alleles at either rs6897932 and/or rs2523506, or any other variant in linkage disequilibrium with rs6897932 or rs2523506, identifies the subject from which the biological sample was obtained as having multiple sclerosis or an increased risk of developing multiple sclerosis, relative to a biological sample from a human subject lacking the risk allele at the SNPs rs2523506 and/or rs6897932; detecting or measuring in the biological sample is defined further as detecting phenotypic differences in the expression of DDX39B protein in a subject suspected of having multiple sclerosis, whereby decreased expression of DDX39B protein in the biological sample identifies the subject from which the biological sample was obtained as having multiple sclerosis or an increased risk of developing multiple sclerosis, relative to a biological sample from a subject not suspected to have multiple sclerosis; or detecting or measuring in the biological sample is defined further as detecting phenotypic differences in the expression of DDX39B protein, whereby decreased expression of DDX39B protein in the biological sample from an individual carrier of the risk allele at rs2523506, or any other variant in linkage disequilibrium with rs2523506, identifies the subject from which the biological sample was obtained as having multiple sclerosis or an increased risk of developing multiple sclerosis, relative to a biological sample from a human subject lacking the risk allele at the SNPs rs2523506. In another aspect, the step of detecting or measuring in the biological sample is a detection of nucleic acids by a hybridization reaction, a polymerase chain reaction, restriction endonuclease digestion analysis, restriction fragment length polymorphism (RFLP) analysis, an amplification reaction, an isothermal amplification reaction, or a multiplex amplification reaction, a polymerase chain reaction (PCR) amplification reaction, a real-time quantitative polymerase chain reaction (qPCR) amplification reaction, a reverse transcriptase PCR (RT-PCR) amplification reaction, primer extension, DNA array technology, a linear amplification technique, a ligation reaction, direct sequencing, a sequencing reaction, or a combination thereof. In another aspect, the step of detecting or measuring in the biological sample is a detection of IL7R or RNA Helicase DDX39B proteins by LUMINEX, ELISA, immunoassay, mass spectrometry, high performance liquid chromatography, two-dimensional electrophoresis, Western blotting, flow cytometry, chemiluminescence immunoassay, a sandwich assay, a precipitation reaction, an immunoprecipitation reaction, a precipitin reaction, a gel diffusion, immunodiffusion assay, an agglutination assay, a fluorescent immunoassay, protein microarray, radioimmunoassay, or antibody microarray. In another aspect, the method further comprises detecting an mRNA for Interleukin-7 receptor (IL7R) exon 6 splice variants in the biological sample. In another aspect, the method further comprises differentiating between a subject having an increased risk of multiple sclerosis or as having multiple sclerosis. In another aspect, the method further comprises detecting DDX39B interaction with ESE2 that promotes inclusion of IL7R exon 6, and decreases sIL7R expression, which is indicative of a reduced risk for multiple sclerosis. In another aspect, the method further comprises detecting the presence of the risk allele at rs2523506 in the 5' UTR of DDX39B, which reduces translation of DDX39B mRNAs and increases MS risk.

In one embodiment, the present invention includes a method of identifying a human subject as having an increased risk of developing an autoimmune disease caused by elevated levels of soluble Interleukin-7 Receptor (sIL7R) and lower levels of an RNA Helicase DDX39B, comprising: obtaining a biological sample from a subject suspected of having an autoimmune disease; and detecting or measuring in the biological sample an amount of a soluble Interleukin-7 receptor (sIL7R) and an amount of an RNA Helicase DDX39B, whereby a higher secretion of sIL7R and a lower expression of DDX39B identifies the subject from which the biological sample was obtained as having an autoimmune disease or having increased risk of developing an autoimmune disease, when compared to a human subject not having an autoimmune disease.

In yet another embodiment, the present invention includes an assay comprising: measuring an interaction between DDX39B rs2523506 and IL7R rs6897932 by: obtaining a biological sample; detecting in the biological sample an amount of a soluble Interleukin-7 receptor (sIL7R) and an amount of an RNA Helicase DDX39B. In one aspect, a higher secretion of sIL7R and/or lower expression of DDX39B identifies the subject from which the biological sample was obtained as having an increased risk of developing an autoimmune disease, when compared to a human subject not having an autoimmune disease. In another aspect, the autoimmune disease is selected from Multiple sclerosis, Type I diabetes, Rheumatoid arthritis, Systemic lupus erythematosus, Atopic dermatitis, Ankylosing spondylitis, Primary biliary cirrhosis, or inflammatory bowel syndromes such as Ulcerative colitis and Crohn's disease. In another aspect, the levels of the sIL7R and RNA Helicase DDX39B are compared to a subject that does not have an autoimmune disease, wherein an increase in sIL7R or a decrease in RNA Helicase DDX39B are indicative of an increase risk of the subject having an autoimmune disease. In another aspect, the step of detecting or measuring in the biological sample is defined further as being selected from: detecting a presence of the risk alleles at SNPs associated with multiple sclerosis in DDX39B and IL7R genes, at least one SNP selected from at least rs6897932 and rs2523506, or any allele in linkage disequilibrium with the DDX39B and IL7R MS risk alleles; a differential expression of IL7R RNA isoforms; a differential expression of IL7R protein isoforms; a differential expression of DDX39B protein; or any combination thereof; detecting or measuring in the biological sample is defined further as detecting allelic variants in DDX39B nucleic acids, which encodes an RNA helicase critical for inclusion of exon 6 in the Interleukin-7 receptor (IL7R) mRNA, whereby the presence of the risk A allele at the SNP rs2523506 in DDX39B exon 1 (5' UTR of DDX39B mRNAs), or the presence of the complementary allele in the opposite strand, or the presence of any other allele in linkage disequilibrium with rs2523506, identifies the subject from which the biological sample was obtained as having multiple sclerosis or having an increased risk of developing multiple sclerosis, relative to a biological sample from a human subject lacking the risk allele at the SNP rs2523506; detecting or measuring in the biological sample is defined further as detecting allelic variants in DDX39B and the Interleukin-7 receptor (IL7R), whereby the presence of the risk A allele at the SNP rs2523506 in DDX39B exon 1 (5' UTR of DDX39B mRNAs) and the presence of the risk C allele at the SNP rs6897932 in IL7R exon 6, or the presence of the complementary allele in the opposite strand, or the presence of any other allele in linkage disequilibrium with at least one of rs2523506 or rs6897932, identifies the subject from which the biological sample was obtained as having multiple sclerosis or an increased risk of developing multiple sclerosis, relative to a biological sample from a human subject lacking the risk allele at the SNPs rs2523506 and/or rs6897932; detecting or measuring in the biological sample is defined further as detecting phenotypic differences in the expression of Interleukin-7 receptor (IL7R) mRNA isoforms, whereby an elevated fraction of IL7R mRNAs that lack exon 6 in the biological sample from an individual carrier of the risk alleles at rs6897932 and rs2523506, or the presence of the complementary allele in the opposite strand, or any other variant in linkage disequilibrium with rs6897932 and/or rs2523506, identifies the subject from which the biological sample was obtained as having multiple sclerosis or an increased risk of developing multiple sclerosis, relative to a biological sample from a human subject lacking the risk allele at the SNPs rs2523506 and/or rs6897932; detecting or measuring in the biological sample is defined further as detecting phenotypic differences in the expression of Interleukin-7 receptor (IL7R) protein isoforms, whereby elevated levels of the soluble form of IL7R (sIL7R) in the biological sample from an individual carrier of the risk alleles rs6897932 and rs2523506, or the presence of the complementary allele in the opposite strand, or any other variant in linkage disequilibrium with rs6897932 or rs2523506, identifies the subject from which the biological sample was obtained as having multiple sclerosis or an increased risk of developing multiple sclerosis, relative to a biological sample from a human subject lacking the risk allele at the SNPs rs2523506 and/or rs6897932; detecting or measuring in the biological sample is defined further as detecting phenotypic differences in the expression of DDX39B protein in a subject suspected of having multiple sclerosis, whereby decreased expression of DDX39B protein in the biological sample identifies the subject from which the biological sample was obtained as having multiple sclerosis or an increased risk of developing multiple sclerosis, relative to a biological sample from a subject not suspected to have multiple sclerosis; or detecting or measuring in the biological sample is defined further as detecting phenotypic differences in the expression of DDX39B protein, whereby decreased expression of DDX39B protein in the biological sample from an individual carrier of the risk allele at rs2523506, or any other variant in linkage disequilibrium with rs2523506, identifies the subject from which the biological sample was obtained as having multiple sclerosis or an increased risk of developing multiple sclerosis, relative to a biological sample from a human subject lacking the risk allele at the SNPs rs2523506. In one aspect, the assay detects or measures in the biological sample is a detection of nucleic acids by a hybridization reaction, a polymerase chain reaction, restriction endonuclease digestion analysis, restriction fragment length polymorphism (RFLP) analysis, an amplification reaction, an isothermal amplification reaction, or a multiplex amplification reaction, a polymerase chain reaction (PCR) amplification reaction, a real-time quantitative polymerase chain reaction (qPCR) amplification reaction, a reverse transcriptase PCR (RT-PCR) amplification reaction, primer extension, DNA array technology, a linear amplification technique, a ligation reaction, direct sequencing, a sequencing reaction, or a combination thereof. In one aspect, the assay detects or measures in the biological sample is a detection of IL7R or proteins RNA Helicase DDX39B by LUMINEX, ELISA, immunoassay, mass spectrometry, high performance liquid chromatography, two-dimensional electrophoresis, Western blotting, flow cytometry, chemiluminescence immunoassay, a sandwich assay, a precipitin reaction, an immunoprecipitation reaction, a gel diffusion immunodiffusion assay, an agglutination assay, a fluorescent immunoassay, protein microarray, radioimmunoassay, or antibody microarray. In another aspect, the assay also comprises a display that shows differentiating between a subject having an increased risk of multiple sclerosis or as having multiple sclerosis. In another aspect, an allelic variant of the DDX39B gene is rs2523506 or any other variant in linkage disequilibrium. In another aspect, the assay detects DDX39B protein binding to ESE2 that promotes inclusion of IL7R exon 6, and decreases sIL7R expression, which is indicative of a reduced risk for multiple sclerosis. In another aspect, the assay detects the presence of the risk allele at rs2523506 in the 5' UTR of DDX39B, which reduces translation of DDX39B mRNAs and increases MS risk.

Yet another embodiment of the present invention includes a kit for measuring an RNA Helicase DDX39B, comprising: a container comprising a first agent for the detection of an amount of an RNA Helicase DDX39B; and instructions for determining the amount of the first agent. In one aspect, the kit further comprises instructions for determining whether the amount of at least the first agent in a biological sample from a subject that has or is suspected of having an autoimmune disease is greater or lower than an amount in a biological sample from a subject that does not have or is not suspected of having an autoimmune disease. In another aspect, the kit further comprises reagents for detection of nucleic acids of the RNA Helicase DDX39B by a hybridization reaction, a polymerase chain reaction, restriction endonuclease digestion analysis, restriction fragment length polymorphism (RFLP) analysis, an amplification reaction, an isothermal amplification reaction, or a multiplex amplification reaction, a polymerase chain reaction (PCR) amplification reaction, a real-time quantitative polymerase chain reaction (qPCR) amplification reaction, a reverse transcriptase PCR (RT-PCR) amplification reaction, primer extension, DNA array technology, a linear amplification technique, a ligation reaction, direct sequencing, a sequencing reaction, or a combination thereof. In another aspect, the kit further comprises reagents for detection of the RNA Helicase DDX39B in the biological sample by LUMINEX, ELISA, immunoassay, mass spectrometry, high performance liquid chromatography, two-dimensional electrophoresis, Western blotting, flow cytometry, chemiluminescence immunoassay, a sandwich assay, a precipitation reaction, an immunoprecipitation reaction, precipitin reaction, a gel diffusion immunodiffusion assay, an agglutination assay, a fluorescent immunoassay, protein microarray, radioimmunoassay, or antibody microarray. In another aspect, the kit further comprises reagents for detection of a second agent, wherein the second agent is a pre-mRNA, RNA, or protein of the soluble IL7R or the membrane IL7R, wherein the detection is at the nucleic acid or protein level.

Yet another embodiment of the present invention includes a method of identifying the activity of an RNA Helicase DDX39B, comprising: obtaining a biological sample; and detecting or measuring in the biological sample an amount of an RNA Helicase DDX39B, its binding, or its activity. In one aspect, the method further comprises measuring an expression of a soluble Interleukin-7 receptor (sIL7R), wherein the combination of a higher secretion of sIL7R and a decrease in the expression or activity of RNA Helicase DDX39B is determined. In another aspect, the amount of an RNA Helicase DDX39B is measured by detecting a ratio of IL7R mRNA isoforms including or excluding exon 6, or a ratio of the resulting IL7R protein isoforms, or a detectable agent under control of the sequences that control splicing of IL7R exon 6. In another aspect, the step of detecting or measuring in the biological sample is detection of nucleic acids of the Interleukin-7 receptor mRNA lacking exon 6 and the RNA Helicase DDX39B by a hybridization reaction, a polymerase chain reaction, restriction endonuclease digestion analysis, restriction fragment length polymorphism (RFLP) analysis, an amplification reaction, an isothermal amplification reaction, or a multiplex amplification reaction, a polymerase chain reaction (PCR) amplification reaction, a real-time quantitative polymerase chain reaction (qPCR) amplification reaction, a reverse transcriptase PCR (RT-PCR) amplification reaction, primer extension, DNA array technology, a linear amplification technique, a ligation reaction, direct sequencing, a sequencing reaction, or a combination thereof. In another aspect, the step of detecting or measuring in the biological sample is a detection of IL7R protein isoforms and RNA Helicase DDX39B protein by LUMINEX, ELISA, immunoassay, mass spectrometry, high performance liquid chromatography, two-dimensional electrophoresis, Western blotting, chemiluminescence immunoassay, a sandwich assay, a precipitation reaction, an immunoprecipitation reaction, precipitin reaction, a gel diffusion immunodiffusion assay, an agglutination assay, a fluorescent immunoassay, protein microarray, radioimmunoassay, or antibody microarray.

Yet another embodiment of the present invention includes a method of treating a subject with an autoimmune disease caused by lower levels of an RNA Helicase DDX39B, comprising: obtaining a biological sample from a subject suspected of having an autoimmune disease; detecting or measuring in the biological sample an amount of an RNA Helicase DDX39B, wherein a patient is elected for treatment if they have a lower expression or activity of the RNA Helicase DDX39B; and selecting a treatment for the subject from any of the currently available treatments, such as, e.g., mitoxatrone, interferon beta-1a, PEG-interferon beta-1a, azathioprine, fingolimod, natalizumab, or methylprednisone.

Yet another embodiment of the present invention includes a method of treating a subject with an autoimmune disease caused by elevated levels of the soluble isoform of interleukin-7 receptor (sIL7R), comprising: obtaining a biological sample from a subject suspected of having an autoimmune disease; detecting or measuring in the biological sample an amount of the soluble interleukin-7 receptor (sIL7R) and Multiple sclerosis risk alleles in DDX39B rs2523506 and IL7R rs6897932, or the complementary allele in the opposite strand, or any other allele in linkage disequilibrium with rs2523506 and/or rs6897932, wherein a patient is elected for treatment if they have a elevated expression of the soluble interleukin-7 receptor (sIL7R) and risk alleles in DDX39B and/or IL7R; and selecting a treatment for the subject from any of the currently available treatments such as, e.g., mitoxatrone, interferon beta-1a, PEG-interferon beta-1a, azathioprine, fingolimod, natalizumab, or methylprednisone.

Yet another embodiment of the present invention includes a method of treating a subject with an autoimmune disease caused by elevated levels of the soluble isoform of interleukin-7 receptor (sIL7R), comprising: obtaining a biological sample from a subject suspected of having an autoimmune disease; detecting or measuring in the biological sample an amount of the soluble interleukin-7 receptor (sIL7R) and an amount of an RNA Helicase DDX39B, wherein a patient is elected for treatment if they have a elevated expression of the soluble interleukin-7 receptor (sIL7R) and lower expression or activity of the RNA Helicase DDX39B; and selecting a treatment for the subject from any of the currently available treatments such as, e.g., mitoxatrone, interferon beta-1a, PEG-interferon beta-1a, azathioprine, fingolimod, natalizumab, or methylprednisone.

BRIEF DESCRIPTION OF THE DRAWINGS

For a more complete understanding of the features and advantages of the present invention, reference is now made to the detailed description of the invention along with the accompanying figures and in which:

FIGS. 1A-1D shows Knockdown of DDX39B in HeLa cells using two independent DDX39B siRNAs (DDX_3 and DDX_4) and a non-silencing control siRNA (NSC). FIG. 1A, Western blot analysis illustrating depletion of DDX39B. FIGS. 1B-1C, RT-PCR analysis of IL7R exon 6 splicing (+E6=exon included; −E6=exon skipped) in transcripts from a reporter minigene (FIG. 1B) or the endogenous gene (FIG. 1C). FIG. 1D shows the quantification of sIL7R secretion by ELISA. FIGS. 1E-1F shows rescue experiments with HeLa cell lines stably expressing siRNA-resistant DDX39B trans-gene, either wild type (FIG. 1E, WT) or helicase mutant (FIG. 1F, D199A), under the control of the tetracycline operator. Top panels illustrate DDX39B western blot analysis, whereas lower panels show RT-PCR analysis of endogenous IL7R transcripts. In all panels the data is shown as mean±s.d., and statistical significance was assessed using Student's t-test (*$p \le 0.0005$;  $p \le 0.005$; * $p \le 0.05$).

FIGS. 3A to 3C show the DDX39B 5' UTR variant rs2523506 displays allele-specific DDX39B protein expression. FIG. 1A is a schematic representation of the DDX39B gene (black), spliced mRNA isoforms (red) and location of MS-associated variants rs2523506, rs2523512 and rs2516478 (asterisks). FIG. 3B shows RT-qPCR quantification of DDX39B mRNA levels in human PBMCs (left), and African (YRI/ESN, middle) and European (IBS, right) LCLs stratified by rs2523506 genotype. Each symbol represents cells from one individual, and red lines indicate median and interquartile range for each group. Samples sizes were: PBMC, CC=32, AC=31, AA=23; YRI/ESN, CC=12, AC=11, AA=2; and IBS, CC=12, AC=12, AA=3. FIG. 3C is a Western blot analysis of DDX39B protein abundance in African (YRI/ESN, left) and European (IBS, right) LCLs stratified by rs2523506 genotype. Panels in FIG. 3C were assembled with different portions of the same gel. Statistical significance of all measurements was assessed using Student's t-test (two-sided; * $p \leq 0.0005$;  $p \leq 0.005$; * $p \leq 0.05$).

FIGS. 4A and 4B show the risk allele of rs2523506 reduces translational efficiency mediated by DDX39B 5' UTRs. FIG. 4A is a schematic representation of the different DDX39B 5' UTR luciferase reporters, which differ by alternative 3'ss in exon 2 and the single nucleotide change at rs2523506 (C/A). FIG. 4B shows the measurements of translational efficiency in transfected HeLa cells. RNA levels and luciferase activity were measured by RT-qPCR and dual Luciferase assays, respectively. Translational efficiency (mean±s.d.) was determined by dividing luciferase activity by RNA levels. Statistical significance was assessed using Student's t-test (two-sided; ** $p \leq 0.005$; * $p \leq 0.05$).

DETAILED DESCRIPTION OF THE INVENTION

Figure 1A:
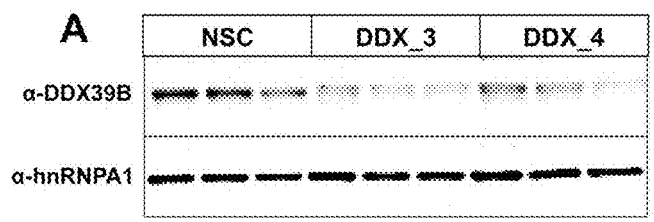
FIGS. 1A to 1F show that DDX39B regulates alternative splicing of IL7R exon 6.
Figure 1B:
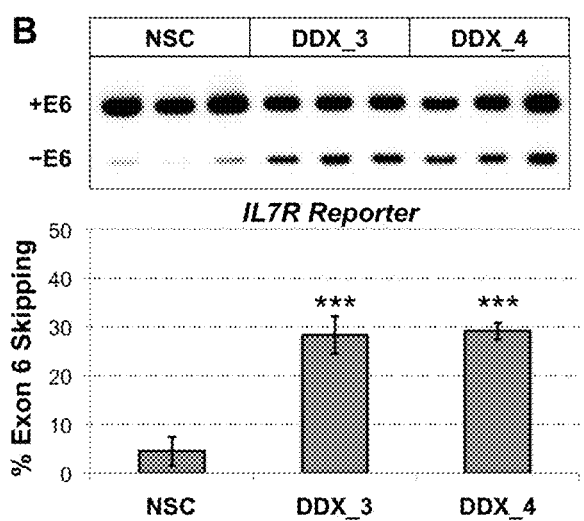

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used herein, the term "multiple sclerosis" refers to a well-characterized neurological disorder caused by demyelination of nerve tissue. The term "multiple sclerosis" or "MS" as used herein includes a disease identified as having a particular art-known status, e.g., relapsing remitting (RRMS), primary progressive (PPMS) and secondary progressive (SPMS), wherein the status of MS as defined according to these and similar terms would be well understood by one of ordinary skill in the art and according to the description provided in the Examples included herewith. RRMS, the most common form, is characterized by onset of symptoms (relapse) followed by complete or nearly complete remission of the symptoms; with this process repeating itself with variable length and severity. The length of time of relapses is variable, as is the remission period. PPMS is characterized by onset of symptoms without subsequent remission, although the severity and constellation of symptoms may vary. SPMS is characterized by initial onset similar to RRMS, with progression such that remission of symptoms no longer happens. Symptoms of MS include, but are not limited to, cognitive deficits, motor weakness (often seen as balance and coordination impairment and ataxia), sensory disturbances (most often pain, numbness, and tingling), and visual disturbances (most often optic neuritis and diplopia). Other examples of autoimmune diseases for use with the present invention include those associated with increased levels of soluble IL7R or genetic association with IL7R, e.g., Type I diabetes, Rheumatoid arthritis, Systemic lupus erythematosus, Atopic dermatitis, Ankylosing spondylitis, Primary biliary cirrhosis, or inflammatory bowel syndromes such as Ulcerative colitis and Crohn's disease.

As used herein, the term "linked" refers to a region of a chromosome that is shared more frequently in family members or members of a population affected by a particular disease or disorder, than would be expected or observed by chance, thereby indicating that the gene or genes or other identified marker(s) within the linked chromosome region contain or are associated with an allele that is correlated with the presence of a disease or disorder, or with an increased or decreased risk of the disease or disorder. Once linkage is established, association studies (linkage disequilibrium) can be used to narrow the region of interest or to identify the marker (e.g., allele or haplotype) correlated with the disease or disorder.

As used herein, the term "linkage disequilibrium" or "LD" refers to the occurrence in a population of two linked alleles at a frequency higher or lower than expected on the basis of the allele frequencies of the individual genes. Thus, linkage disequilibrium describes a situation where alleles occur together more often than can be accounted for by chance, which often indicates that the two alleles are physically close on a DNA strand.

As used herein, the term "genetic marker" refers to a region of a nucleotide sequence (e.g., in a chromosome) that is subject to variability (i.e., the region can be polymorphic for a variety of alleles). For example, a single nucleotide polymorphism (SNP) in a nucleotide sequence is a genetic marker that is polymorphic for two (or in some cases, three or four) alleles. SNPs can be present within a coding sequence of a gene, within noncoding regions of a gene (e.g., intron) and/or in an intergenic region (e.g., between genes). A SNP in a coding region in which both allelic forms lead to the same polypeptide sequence is termed synonymous and if a different polypeptide sequence is produced, the alleles of that SNP are non-synonymous. SNPs that are not in protein coding regions can still have effects on transcription factor binding, RNA splicing, RNA localization, RNA structure, mRNA translation, microRNA binding, mRNA stability and/or the sequence of the non-coding RNA.

Other examples of genetic markers of this invention can include but are not limited to haplotypes (i.e., combinations of alleles), microsatellites, restriction fragment length polymorphisms (RFLPs), repeats (i.e., duplications), insertions, deletions, etc., as are well known in the art.

In the present invention, the term genetic marker is also used to describe the phenotypic effects of the alleles identified herein as associated with MS; including IL7R mRNA comprising or lacking exon 6, soluble IL7R (sIL7R) protein and membrane bound IL7R protein, and RNA helicase DDX39B protein, as described herein.

As used herein, the term "allele" refers to one of two or more alternative forms of a nucleotide sequence at a given position (locus) on a chromosome. Usually alleles are nucleotide sequences in the coding sequence of a gene, but sometimes the term is used to refer to a nucleotide sequence in a non-coding sequence. An individual's genotype for a given gene is the set of alleles it happens to possess.

As used herein, the term "haplotype" refers to a set of single nucleotide polymorphisms (SNPs) on a single chromatid that are statistically associated. It is thought that these associations, and the identification of a few alleles of a haplotype block, can unambiguously identify most other polymorphic sites in its region. Such information is very valuable for investigating the genetics behind common diseases and is collected by the International HapMap Project. The term "haplotype" is also commonly used to describe the genetic constitution of individuals with respect to one member of a pair of allelic genes; sets of single alleles or closely linked genes that tend to be inherited together.

A "subject" in this invention is any animal that is susceptible to multiple sclerosis as defined herein and can include, for example, humans, as well as animal models of MS such as non-human primates (i.e. macaque, marmoset, etc.), rodents (mouse, rat, etc.) or other animals that can be subjected to the experimental autoimmune encephalomyelitis (EAE) or other MS disease models. Subjects of this invention can be male or female. A subject may be identified as being at risk of developing MS or as having or suspected of having MS by the use of genotypic and/or phenotypic screening.

As used herein, the term "nucleic acids" refers to both RNA and DNA, including cDNA, genomic DNA, mRNA, synthetic (e.g., chemically synthesized) DNA and chimeras of RNA and DNA. The nucleic acid can be double-stranded or single-stranded. Where single-stranded, the nucleic acid can be a sense strand or an antisense strand. The nucleic acid can be synthesized using nucleotide analogs or derivatives (e.g., inosine or phosphorothioate nucleotides). Such nucleotides can be used, for example, to prepare oligonucleotides that have altered base-pairing abilities or increased resistance to nucleases.

As used herein, the term "isolated nucleic acid" refers to a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. Standard recombinant DNA methodologies are used to obtain nucleic acids encoding nucleic acids, peptides, or proteins, or to incorporate nucleic acids into recombinant expression vectors and introduce the vectors into host cells. In general, the practice of the present invention employs, unless otherwise indicated, conventional techniques of chemistry, molecular biology, recombinant DNA technology, immunology (especially, e.g., antibody technology), and standard techniques of nucleic acid isolation and/or polypeptide isolation. See, e.g., Sambrook, Fritsch and Maniatis, Molecular Cloning: Cold Spring Harbor Laboratory Press (1989); Antibody Engineering Protocols (Methods in Molecular Biology), 510, Paul, S., Humana Pr (1996); Antibody Engineering: A Practical Approach (Practical Approach Series, 169), McCafferty, Ed., Irl Pr (1996); Antibodies: A Laboratory Manual, Harlow et al., C.S.H.L. Press, Pub. (1999); and Current Protocols in Molecular Biology, eds. Ausubel et al., John Wiley & Sons (1992), relevant portions incorporated herein by reference.

As used herein, the term "isolated" refers to a nucleic acid or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid or polypeptide that is not naturally occurring as a fragment and would not be found in the natural state. Likewise, an isolated cell refers to a cell that is separated from other cells and/or tissue components with which it is normally associated in its natural state.

As used herein, the term "oligonucleotide" refers to a nucleic acid sequence of at least about six nucleotides to about 100 nucleotides, for example, about 15 to 30 nucleotides, or about 20 to 25 nucleotides, which can be used, for example, as a primer in a PCR amplification or as a probe in a hybridization assay or in a microarray. Oligonucleotides can be natural or synthetic, e.g., DNA, RNA, modified backbones, etc. Peptide nucleic acids (PNAs) can also be used as probes in the methods of this invention. The present invention further provides fragments or oligonucleotides of the nucleic acids of this invention, which can be used as primers or probes. Thus, in some embodiments, a fragment or oligonucleotide of this invention is a nucleotide sequence that is at least, for example 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, 750, 800, 850, 900, 1000, 1500, 1750 or 1800 contiguous nucleotides of a nucleic acid of this invention (e.g., the genomic sequence of the IL7R chain gene; the coding sequence or mRNA sequence GenBank Accession No. NM002185 that encodes the IL7R chain protein (relevant sequence incorporated herein by reference, if more that one version is available, that available on the date of this application was used), GenBank Accession No. NP002176, with and without exon 6 (relevant sequence incorporated herein by reference, if more that one version is available, that available on the date of this application was used) encoding membrane bound or soluble IL7R chain, respectively, and as taught in U.S. Pat. No. 8,158,344, relevant portions and sequences incorporated herein by reference. Such fragments or oligonucleotides can be detectably labeled or modified, for example, to include and/or incorporate a restriction enzyme cleavage site or a fluorophore for imaging when employed as a primer in an amplification (e.g., PCR) assay.

The present invention can also include the detection of sIL7R or RNA Helicase DDX39B proteins. Non-limiting examples of protein detection methods to detect or measure sIL7R or RNA Helicase DDX39B include, e.g., LUMINEX, ELISA, immunoassay, mass spectrometry, high performance liquid chromatography, two-dimensional electrophoresis, Western blotting, chemiluminescence immunoassay, a sandwich assay, a precipitation reaction, an immunoprecipitation reaction, a precipitin reaction, a gel diffusion immunodiffusion assay, an agglutination assay, a fluorescent immunoassay, protein microarray, radioimmunoassay, or antibody microarray.

As used herein, the term "biological sample" refers to a sample obtained from a biological subject, including sample of biological tissue or fluid origin including, but limited to, body fluids (e.g., blood, blood plasma, serum, or urine), secreted bodily fluids such as tears, sputum, rectal or vaginal secretions, or fluids or samples obtained by crossing the skin such as peritoneal fluids, cerebrospinal fluids, biopsies, organs, tissues, fractions, and cells isolated from the subject. Biological samples may also include extracts from a biological sample that may comprise proteins and/or nucleic acids.

The present invention can also include the detection of sIL7R or RNA Helicase DDX39B nucleic acids. Non-limiting examples of nucleic acid methods to detect or measure sIL7R or RNA Helicase DDX39B include, e.g., a hybridization reaction, a polymerase chain reaction, restriction endonuclease digestion analysis, Restriction Fragment Length Polymorphism (RFLP) analysis, an amplification reaction, an isothermal amplification reaction, or a multiplex amplification reaction, a polymerase chain reaction (PCR) amplification reaction, a real-time quantitative polymerase chain reaction (qPCR) amplification reaction, a reverse transcriptase PCR (RT-PCR) amplification reaction, primer extension, DNA array technology, a linear amplification technique, a ligation reaction, direct sequencing, a sequencing reaction, or a combination thereof.

In the methods described herein, the detection of a genetic marker of this invention (e.g., an allele and/or a haplotype) in a subject can be carried out according to methods well known in the art. For example, nucleic acid can be obtained from any suitable sample from the subject that will contain nucleic acid and the nucleic acid can then be prepared and analyzed according to well-established protocols for the presence of genetic markers according to the methods of this invention. In some embodiments, analysis of the nucleic acid can be carried by amplification of the region of interest according to amplification protocols well known in the art (e.g., polymerase chain reaction, ligase chain reaction, strand displacement amplification, transcription-based amplification, self-sustained sequence replication (3 SR), Qβ replicase protocols, nucleic acid sequence-based amplification (NASBA), repair chain reaction (RCR) and boomerang DNA amplification (BDA), etc.). The amplification product can then be visualized directly in a gel by staining or the product can be detected by hybridization with a detectable probe. When amplification conditions allow for amplification of all allelic types of a genetic marker, the types can be distinguished by a variety of well-known methods, such as hybridization with an allele-specific probe, secondary amplification with allele-specific primers, by restriction endonuclease digestion, and/or by electrophoresis. Thus, the present invention further provides oligonucleotides for use as primers and/or probes for detecting and/or identifying genetic markers, or direct DNA and/or RNA sequencing according to the methods of this invention.

The genetic markers of this invention are correlated with multiple sclerosis as described herein according to methods well known in the art and as disclosed in the Examples provided herein for correlating genetic markers with various phenotypic traits, including disease states and pathological conditions and levels of risk associated with developing a disease or pathological condition. In general, identifying such correlation involves conducting analyses that establish a statistically significant association and/or a statistically significant correlation between the presence of a genetic marker or a combination of markers and the phenotypic trait in the subject. An analysis that identifies a statistical association (e.g., a significant association) between the marker or combination of markers and the phenotype establishes a correlation between the presence of the marker or combination of markers in a subject and the particular phenotype being analyzed.

In some embodiments of the methods of this invention, particular alleles of the genetic markers are identified as being correlated with multiple sclerosis or with an increased risk of developing multiple sclerosis. Furthermore, any other allele identified to be highly statistically correlated with this allele can be used to identify a subject at increased risk of developing MS, such as, a C allele at SNP rs1494555, a C allele at SNP rs987107, an A allele at SNP rs987106, as well as a haplotype comprising any combination thereof in addition to the C allele at SNP rs6897932, or any other SNP in LD with rs6897932. Other SNPs of relevance to the present invention include rs2523506 (exon 1, 5' UTR of DDX39B mRNA), rs2523512 (intron 3) and rs2516478 (intron 9), or any other SNP in LD with rs2523506.

Furthermore, as described in the Examples section herein, the phenotypic result of the presence of the C allele at SNP rs6897932 is an increase in the production of an IL7R mRNA lacking exon 6, thereby increasing production of the soluble form of the IL7R protein (sIL7R), in combination with the detection of presence of risk alleles in the DDX39B gene, or a decrease in expression or activity of RNA Helicase DDX39B.

The present inventors further strengthen herein the link between IL7R exon 6 splicing and MS pathogenesis by demonstrating that trans-acting factors that control splicing of the exon are candidate genes for MS susceptibility and treatment. Indeed, the present inventors show herein that the RNA helicase DDX39B (previously known as UAP56 and BAT1) is a potent activator of IL7R exon 6, and consequently a repressor of sIL7R, and establish strong genetic association of DDX39B with MS risk. Furthermore, the present inventors show herein that the variant rs2523506 (C/A, where A is the risk allele) in the 5' UTR of DDX39B mRNA lowers DDX39B protein levels via reduced translation of DDX39B mRNAs, and in doing so it increases MS risk. Critical for the method proposed here, this DDX39B variant showed strong genetic and functional epistasis with rs6897932 in IL7R exon 6, wherein carriers of the risk alleles at both loci are at greater risk to develop the disease, most likely due to increased skipping of exon 6 and up-regulation of sIL7R.

To date, variants within the Human Leukocyte Antigen (HLA) genes exhibit the greatest effect on MS risk and are considered the primary genetic drivers of MS (International Multiple Sclerosis Genetics et al., 2015; Patsopoulos et al., 2013). In contrast, the hundreds of variants outside of HLA genes identified so far have only small effects on MS risk. Importantly, the joint genotypic effect of this epistatic interaction between IL7R rs6897932 and DDX39B rs2523506 is much greater than any other non-HLA risk variant and comparable to the effect of HLA variants. Therefore, a method is taught herein to identify individuals at high risk to develop the disease based on genetic screening for allelic variants in IL7R rs6897932 and DDX39B rs2523506 and phenotypic screening of IL7R mRNA and protein isoform expression.

Multiple Sclerosis (MS) is an autoimmune disorder where T cells attack neurons in the central nervous system (CNS) leading to demyelination and neurological deficits. A driver of increased MS risk is the soluble form of the interleukin-7 receptor alpha chain gene (sIL7R), produced by alternative splicing of IL7R exon 6. Here, the inventors identified the RNA helicase DDX39B as a potent activator of this exon and consequently a repressor of sIL7R, and found strong genetic association of DDX39B with MS risk. Indeed, the inventors show herein that a genetic variant in the 5' UTR of DDX39B reduces translation of DDX39B mRNAs and increases MS risk. Importantly, this DDX39B variant showed strong genetic and functional epistasis with allelic variants in IL7R exon 6. This study establishes the occurrence of biological epistasis in humans and provides mechanistic insight into the regulation of IL7R exon 6 splicing and its impact on MS risk.

MS is characterized by self-reactive T cell mediated damage to neuronal myelin sheaths in the CNS that leads to axonal demyelination, neuronal death and progressive neurological dysfunction. This breach of immunological tolerance is thought to originate from complex interactions between environmental and genetic factors. Addressing the latter, the inventors the inventors and others uncovered a role for IL7R in MS susceptibility (Gregory et al., 2007; International Multiple Sclerosis Genetics et al., 2007; Lundmark et al., 2007). Together with the common gamma chain ($\gamma_c$), IL7R forms a functional cell surface receptor for IL7, which is essential for survival, proliferation, maintenance and homeostasis of T cells (Fry and Mackall, 2005; Mazzucchelli and Durum, 2007), and may also be required for optimal TCR-mediated activation of CD4$^+$ T cells (Lawson et al., 2015) thought to drive the initial inflammatory phase of MS (Sospedra and Martin, 2005). The skilled artisan will recognize that IL7R refers to the membrane bound form of IL7R (also referred to as mIL7R), which is in contrast to a soluble form of IL7R referred to as sIL7R, which is the subject of the present invention. Importantly, IL7R expression is precisely and dynamically controlled throughout lymphopoiesis and upon T cell activation (Alves et al., 2008; Mazzucchelli and Durum, 2007; Munitic et al., 2004; Park et al., 2004), and its modulation has profound effects on immunological function as knockout of IL7R in mice and loss-of-function mutations in humans cause lymphopaenia and severe combined immunodeficiency (Maraskovsky et al., 1996; Peschon et al., 1994; Puel et al., 1998; Roifman et al., 2000). Relevant to the establishment of self-tolerance, dynamic regulation of IL7R throughout lymphopoiesis seems critical for selection of self-tolerant T cells (Dooms, 2013).

The single nucleotide polymorphism (SNP) rs6897932 within exon 6 of IL7R is strongly and reproducibly associated with MS, where the C allele of the variant is associated with elevated risk (Gregory et al., 2007; International Multiple Sclerosis Genetics et al., 2007; Lundmark et al., 2007). This variant introduces a non-synonymous threonine to isoleucine change at amino acid position 244, but this change does not appear to alter IL7 signaling (unpublished results). Importantly, the inventors showed that the risk allele enhances skipping of exon 6 (Evsyukova et al., 2013; Gregory et al., 2007), increasing the fraction of mRNAs that code for a secreted form of the receptor (sIL7R), and this correlates with increased plasma levels of sIL7R (Hoe et al., 2010; Lundstrom et al., 2013). Elevated levels of sIL7R have been shown to exacerbate the severity of experimental autoimmune encephalomyelitis (EAE), a mouse model of MS, presumably by enhancing the bioactivity or bioavailability of IL7 (Lundstrom et al., 2013). These results directly link alternative splicing of IL7R exon 6 to the pathogenesis of MS.

To better understand how splicing of IL7R exon 6 is regulated, the inventors pursued the discovery of both cis-acting elements and trans-acting factors controlling splicing of the exon. Previously the inventors identified several important cis-acting elements, among them a critically important exonic splicing enhancer (ESE2), immediately downstream of rs6897932, whose mutation (ΔESE2) inhibited inclusion of exon 6 (Evsyukova et al., 2013). By combining RNA affinity chromatography with mass spectrometry, the inventors discovered factors interacting with exon 6 and flanking sequences (Evsyukova et al., 2013) and factors that required ESE2 to bind (Galarza-Munoz et al., 2017). The inventors showed that knockdown of one of these factors, the DEAD Box Polypeptide 39B (DDX39B, also known as UAP56/BAT1), increased IL7R exon 6 skipping in cell lines and in primary CD4$^+$ T cells, and up-regulated sIL7R secretion. This is relevant in vivo since the inventors established that genetic variants within the DDX39B locus were associated with increased genetic risk of MS. The inventors further demonstrated that the risk allele of one of these variants, rs2523506, reduces DDX39B protein level by diminishing the efficiency of DDX39B mRNA translation. Importantly, the increased risk associated with this variant showed significant epistasis with rs6897932 in IL7R. This study demonstrated the occurrence of genetic and functional epistasis of two MS risk loci in humans and provides a mechanistic explanation for the regulation of IL7R alternative splicing as a driver of MS risk. Furthermore, considering that variants in both IL7R and DDX39B have been associated with other autoimmune diseases (Anderson et al., 2011; Cheong et al., 2001; Degli-Esposti et al., 1992; Nakamura et al., 2012; Paternoster et al., 2012; Quinones-Lombrana et al., 2008; Todd et al., 2007), the results of this study could have a broader impact on shared mechanisms in autoimmunity.

DDX39B is a potent activator of IL7R exon 6. To identify trans-acting factors controlling splicing of IL7R exon 6, the inventors conducted an unbiased proteomic screen using RNA affinity chromatography and mass spectrometry. Using different sets of IL7R exon 6 RNAs and HeLa nuclear extracts the inventors identified a total of 89 candidate trans-factors (Evsyukova et al., 2013). Importantly, the inventors showed that both HeLa and Jurkat T cells recapitulate the SNP rs6897932- and ESE2-dependent changes in IL7R exon 6 splicing, implying exon 6 is similarly regulated in HeLa and T cells. In the experiments presented here, the inventors used RNAs encompassing the first 40 nucleotides (nt) of exon 6, either wild type or ΔESE2 (both containing the C allele of rs6897932), to identify factors binding in the vicinity of rs6897932 and the critical ESE2. The inventors identified 66 candidate factors with these short RNAs, 12 of which showed dependency on ESE2 (Table 1). The two top candidates whose binding was ESE2-dependent were the microtubule-associated protein 4 (MAP4) and the RNA helicase DDX39B. Functional studies ruled out a role for MAP4 in IL7R exon 6 splicing (data not shown) and thus the inventors focused on DDX39B.

TABLE 1

Trans-acting factors exhibiting dependence on ESE2 for binding to IL7R exon 6 (Related to FIGS. 1A to 1F).

| Protein | No RNA | Wild type | ΔESE2 | Fold-change |
|---|---|---|---|---|
| Microtubule-associated protein 4 (MAP4) | 1 | 7 | 1 | −7.0 |
| RNA helicase DDX39B | 0 | 5 | 1 | −5.0 |
| 40S Ribosomal protein SA | 1 | 4 | 1 | −4.0 |
| 14-3-3 protein gamma | 0 | 3 | 1 | −3.0 |
| hnRNP R | 0 | 3 | 1 | −3.0 |
| Scaffold attachment factor B1 | 0 | 5 | 2 | −2.5 |
| snRNP E | 0 | 4 | 2 | −2.0 |
| 60S Ribosomal Protein L8 | 0 | 2 | 1 | −2.0 |
| Prothymosin alpha | 1 | 2 | 1 | −2.0 |
| 60S Ribosomal Protein L7 | 0 | 2 | 1 | −2.0 |
| 40S Ribosomal protein S3 | 0 | 2 | 1 | −2.0 |
| 40S Ribosomal Protein S20 | 0 | 2 | 1 | −2.0 |

Trans-acting factors were pulled-down from HeLa nuclear extracts by Tobramycin RNA affinity chromatography using an RNA spanning the first 40 nt of IL7R exon 6, either wild type or mutant ESE2 (ΔESE2), and a no RNA control (Evsyukova et al., 2013). RNA-Protein complexes were eluted with excess tobramycin and the bound proteins were identified by mass spectrometry. The table indicates the total number of unique peptides corresponding to each factor that were pulled-down with no RNA control, wild type or ΔESE2 RNAs in two independent experiments, and the fold-change decrease in binding observed with mutation of ESE2.

Figure 1C:
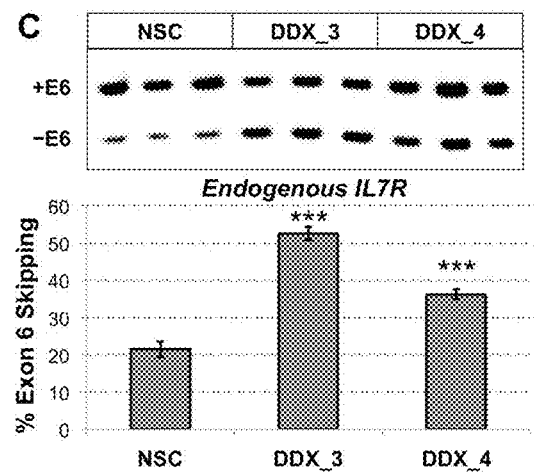
Figure 1D:
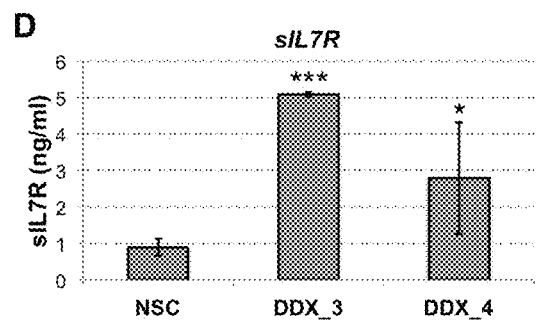
Figure 1E:
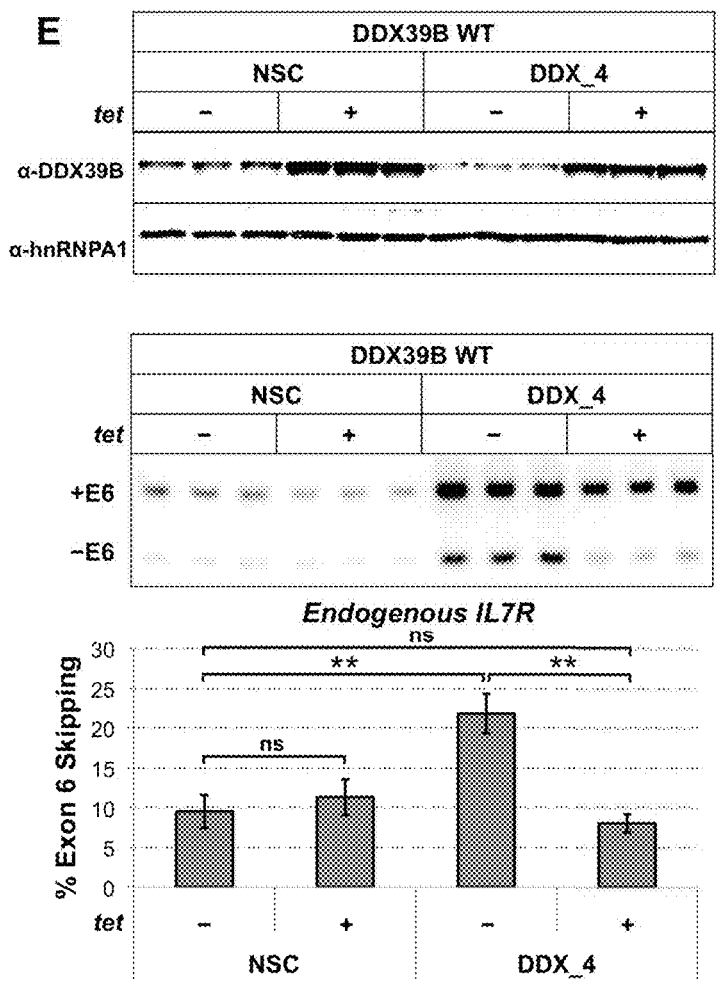
Figure 1F:
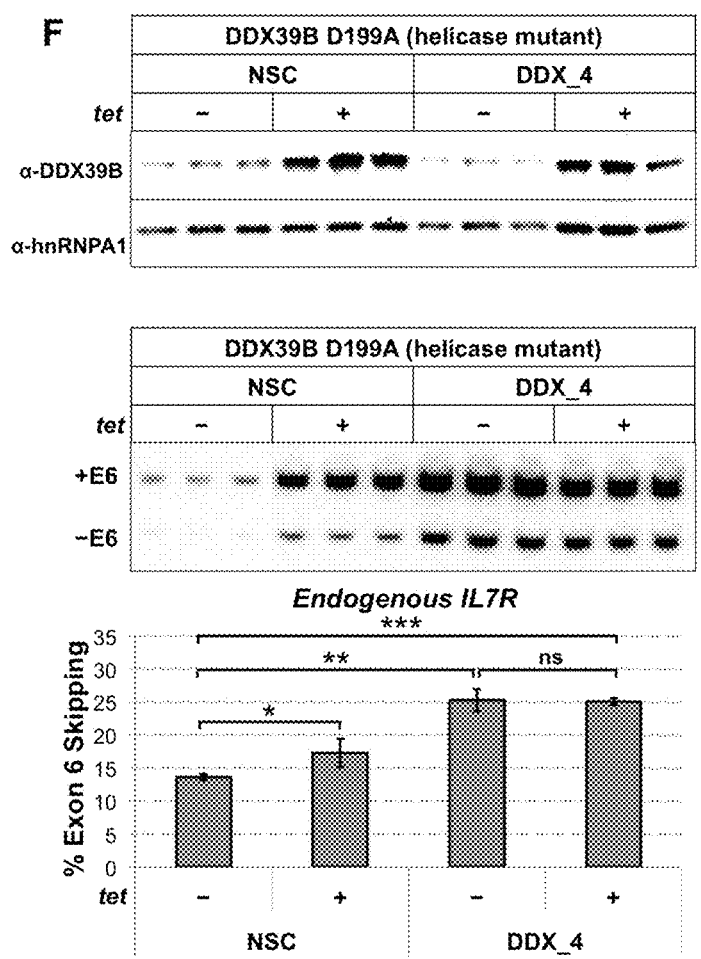

To determine whether DDX39B regulates splicing of IL7R exon 6, the inventors silenced its expression in HeLa cells using two independent siRNAs (FIG. 1A), and determined the impact on exon 6 splicing in transcripts from both an IL7R reporter minigene and the endogenous IL7R gene. Knockdown of DDX39B caused a significant increase in exon 6 skipping in transcripts from both the minigene (FIG. 1B) and endogenous gene (FIG. 1C). This effect cannot be explained by differential effects of DDX39B on stability of IL7R transcript isoforms as both isoforms decayed with similar rates in control and DDX39B-depleted cells (data not shown). Importantly, the inventors were able to rescue exon 6 splicing in endogenous IL7R transcripts by complementing DDX39B-depleted cells with a siRNA-resistant cDNA trans-gene encoding wild type DDX39B (FIG. 1E) but not a helicase-defective mutant (FIG. 1F). In these experiments, DDX39B depletion also led to elevated abundance of overall IL7R transcripts (confirmed by RT-qPCR; data not shown), which may be a secondary effect of DDX39B depletion, as it appeared only at later time points during knockdown. Similar rescue experiments conducted with an ESE2 mutant reporter strongly suggested there is no DDX39B effect in the absence of this ESE (FIG. S2). These results indicated the splicing phenotype observed upon transfection of DDX39B siRNAs was specifically driven by DDX39B protein depletion rather than an off-target effect of the siRNAs, and that DDX39B requires its helicase activity and an intact ESE2 to activate exon 6 inclusion. Most importantly, the inventors showed that DDX39B knockdown elevated the secretion of sIL7R (FIG. 1D).

Previous studies suggested that DDX39B interacts with U2AF65 in the vicinity of the branchpoint sequence (BP) to promote constitutive pre-mRNA splicing (Fleckner et al., 1997; Shen et al., 2008; Shen et al., 2007). Since the data revealed a role for DDX39B in alternative splicing, the inventors wondered whether DDX39B silencing affects other alternative splicing events. A pilot investigation in HeLa cells identified 75 alternative splicing events that were changed upon DDX39B depletion, and a significant fraction were exon skipping events, consistent with DDX39B acting as a splicing activator. The inventors also investigated how sensitive inclusion of IL7R exon 6 was to silencing of other RNA helicases. Knockdown of DDX5, a helicase implicated in both transcriptional and post-transcriptional control (Huang et al., 2015), and DDX23, the U5 snRNP-associated human homologue of PRP28 (Teigelkamp et al., 1997), caused small effects in exon 6 skipping, whereas knockdown of DDX17, another RNA helicase with alternative splicing activity (Honig et al., 2002) had no effect (FIG. S3). These results suggest that IL7R exon 6 is particularly sensitive to DDX39B levels and indicate that this RNA helicase impacts multiple alternative splicing events. Collectively, these experiments demonstrated that DDX39B is an important activator of IL7R exon 6 splicing, and a potent repressor of sIL7R.

DDX39B is genetically associated with MS risk. To determine whether genes encoding regulators of IL7R exon 6 are associated with MS susceptibility, the inventors performed parallel genetic association analyses of autosomal genes encoding candidate trans-acting factors identified in the proteomics screen. When candidate factors form part of macromolecular complexes, the inventors added the other components of such complexes for a total of 116 candidate genes. The inventors combined data from six genetic cohorts of non-overlapping subjects of European descent from previously published meta-analyses (Patsopoulos et al., 2011), which included 4,088 MS cases and 7,444 controls. Genotype data were available for 4,882 SNPs in 96 of the 116 candidate genes (minor allele frequency (MAF)≥1%; imputation information score ≥80%). Variants within +/−10 kilobases (kb) of candidate genes were analyzed using meta-analytic logistic regression models adjusted for population stratification and cohort origin. A total of 58 SNPs reached genome-wide statistical significance ($p \leq 5.0 \times 10^{-8}$), all of which resided within the DDX39B gene locus.

Figure 2:
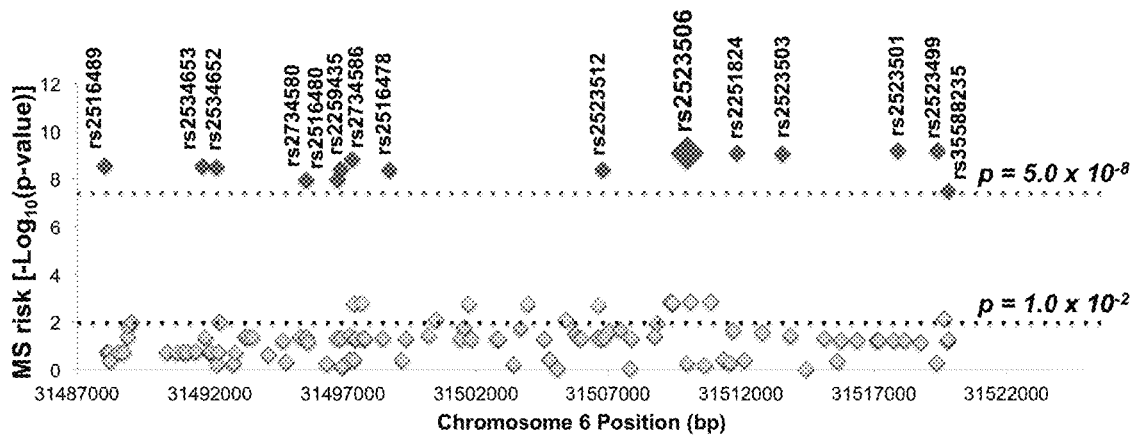
FIG. 2 is a map that shows the variants within or adjacent to the DDX39B locus strongly associated with MS risk. Each diamond represents a variant analyzed, and the color of the diamonds indicates no association (gray), marginal association (yellow) or strong association (red) with MS risk. The variant rs2523506 is indicated with a larger diamond (see FIG. 3). Black and blue dotted lines indicate thresholds for marginal ($p \le 1.0 \times 10^{-2}$) and strong ($p \le 5.0 \times 10^{-8}$) association, respectively. The location of the four genes present in this region of chromosome 6 is illustrated at the bottom.
Figure 2:
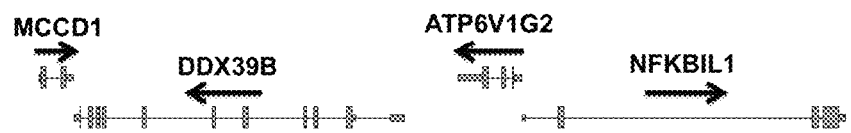

The DDX39B gene is located within the major histocompatibility complex (MHC). This region harbors the human leukocyte antigen (HLA) genes, the primary genetic drivers of MS susceptibility (International Multiple Sclerosis Genetics et al., 2015; Patsopoulos et al., 2013), and exhibits extended linkage disequilibrium (LD) (de Bakker et al., 2006). Accordingly, it was imperative to establish whether DDX39B variants were associated with increased MS risk independent of the known HLA risk factors, rather than reporting on HLA risk variants in LD. To this end, the inventors further refined the genetic model to adjust for all known HLA MS risk variants: HLA-DRB1*15:01, HLA-DRB1*03:01, HLA-DRB1*13:01, HLA-DRB1*04:04, HLA-DRB1*04:01, HLA-DRB1*14:01, HLA-A*02:01, rs9277489, HLA-B*37:01, and HLA-B*38:01 (hereafter referred to as HLA-adjusted model). There were 15 variants in DDX39B with strong association with MS risk after correction for HLA risk alleles ($p \leq 5.0 \times 10^{-8}$) (FIG. 2). The inventors used this HLA-adjusted model to inform subsequent functional analyses of DDX39B variants displaying strong association with MS risk. While there were four genes within the associated region (FIG. 2), the functional experiments demonstrating robust repression of sIL7R by DDX39B (FIGS. 1A to 1F) strongly suggested that DDX39B drives this association and reduces MS risk by decreasing sIL7R expression.

Figure 3A:
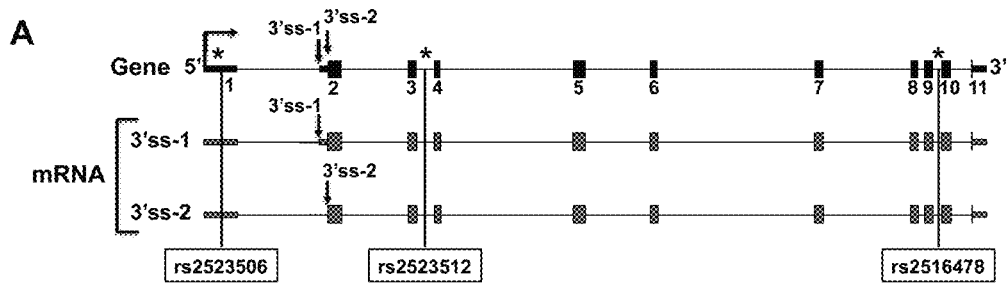

Allele-specific DDX39B protein expression. The inventors next investigated whether any of the DDX39B MS-associated variants altered its activity. Because none of the associated variants are located in the coding region, the inventors hypothesized that the functional SNP(s) act by regulating DDX39B expression. Three of the associated variants are located within the transcriptional unit of the gene: rs2523506 (exon 1), rs2523512 (intron 3) and rs2516478 (intron 9) (FIG. 3A). The inventors tested whether rs2523512 in intron 3 could impact splicing of exons 3 and 4, and found no effect (data not shown). The inventors next focused on rs2523506 located in the 5' UTR of DDX39B transcripts where it could alter mRNA levels and/or their translation efficiency. The inventors first asked whether rs2523506 genotype correlated with changes in DDX39B transcript levels in peripheral blood mononuclear cells (PBMCs) isolated from relapsing-remitting MS patients and healthy controls. Quantification of the DDX39B mRNAs showed that they did not (FIG. 3B, left), indicating that MS risk association could not be explained by decreased DDX39B mRNA levels.

The inventors next asked whether rs2523506 could influence translational efficiency of DDX39B mRNAs, which would lead to differential abundances of DDX39B protein. To address this, the inventors initially mined a proteomics database where relative protein abundances were quantified for 5,953 genes in lymphoblastoid cell lines (LCLs) (Wu et al., 2013). The inventors found reduced DDX39B protein levels in cell lines heterozygous at rs2523506 (AC) compared to cells homozygous for the protective allele (CC) in LCLs from an African population (Yoruba in Ibadan, Nigeria [YRI]). Unfortunately, no data were available for the homozygous risk allele (AA). This correlation with DDX39B levels was not detected in LCLs from an European population (Utah residents with ancestry from northern and western Europe [CEU]), which also lacked data for the AA genotype, suggesting that regulation of DDX39B levels is complex and may be differentially modified by other loci or non-genetic factors between these LCL populations. These data demonstrate that the risk allele of rs2523506 can reduce DDX39B protein expression.

Figure 3B:
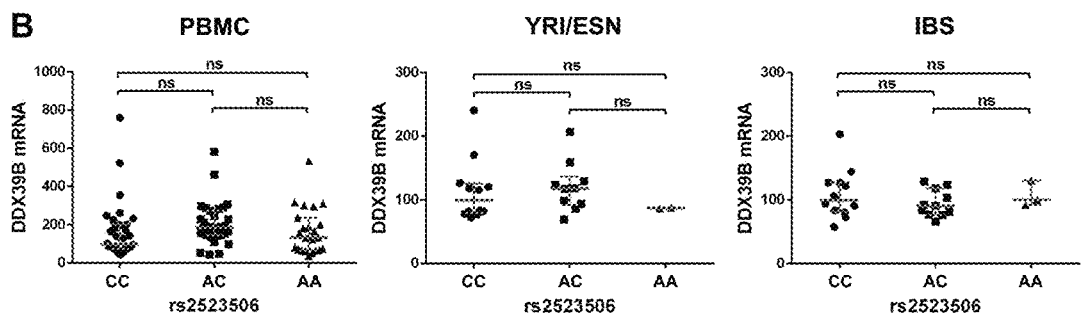

To rigorously test the correlation between DDX39B protein levels and rs2523506 alleles the inventors experimentally analyzed 25 LCLs of African origin (12 CC, 11 AC and 2 AA) and 27 LCLs of European origin (12 CC, 12 AC and 3 AA). The inventors used LCLs from two African populations, YRI and Esan in Nigeria (ESN), which were entirely distinct from the previously analyzed cell lines (Wu et al., 2013), thereby allowing the inventors to test for replication of the correlation between rs2523506 and DDX39B protein levels. Given the lack of correlation in CEU LCLs and concerns associated with these cell lines being more extensively passaged than the other LCLs (Yuan et al., 2015), the inventors analyzed LCLs established more recently from Iberian populations in Spain (IBS). The inventors first checked levels of DDX39B mRNAs and, similar to findings in PBMCs, found no significant differences in DDX39B mRNA levels by rs2523506 genotype in either the African (YRI/ESN) or European (IBS) LCLs (FIG. 3B). Additionally, the inventors assessed whether rs2523506 altered expression of genes in the vicinity of DDX39B (MICB, ATP6V1G2, NFKBIL1, LTA, TNF and LTB) in the African LCLs and found no difference in RNA levels by rs2523506 genotype. Furthermore, silencing of vicinal genes that were expressed in HeLa cells had no effect on IL7R exon 6 splicing. These analyses indicated rs2523506 does not affect RNA levels of other genes within the associated region, consistent with this variant driving MS risk via its impact on DDX39B protein expression.

The inventors next analyzed DDX39B protein levels by western blot in both populations of LCL (FIG. 3C). Analysis in the African LCLs revealed a dose-dependent correlation of the risk allele of rs2523506 with reduced DDX39B protein levels, with approximately 25% reduction in AC lines and 50% reduction in AA lines compared to CC lines (FIG. 3C, left). The inventors observed a similar correlation in DDX39B protein levels in the European LCLs, albeit to a lesser extent, and statistically significant when comparing CC and AA lines (FIG. 3C, right). Thus, the inventors concluded that the A risk allele of rs2523506 is associated with decreased DDX39B protein levels. Moreover, given that DDX39B mRNA levels were unaltered by rs2523506 genotype, the inventors hypothesized that the rs2523506 risk allele functions by reducing the DDX39B mRNA translation.

rs2523506 controls translation efficiency of DDX39B mRNAs. To investigate whether rs2523506 influences translational efficiency of DDX39B transcripts, the inventors generated luciferase reporters containing the DDX39B 5' UTR variants. In addition to the alternative alleles of rs2523506 (C/A), the 5' UTR of DDX39B transcripts is further modified by alternative 3' splice sites (3'ss) within exon 2 (3'ss-1 and 3'ss-2 in FIG. 3A). Therefore, to precisely mimic the naturally occurring DDX39B 5' UTR variants, the inventors generated reporters reflecting the use of the different 3'ss in exon 2 and the alternative alleles of rs2523506 (C/A) (FIG. 4A). These reporters were transiently transfected into HeLa cells together with a Firefly luciferase (F-Luc) transfection control, and translational efficiency was determined by quantifying mRNA and luciferase levels, each normalized to the F-Luc control. This analysis revealed approximately 20-30% reduction in translational efficiency of the reporters containing the A risk allele compared to the C allele (FIG. 4B). Importantly, this effect of rs2523506 on translational efficiency largely explains the reduction in DDX39B protein levels observed between CC and AA LCLs. Taken together with the results in FIGS. 3A to 3C, the inventors concluded that the A risk allele of rs2523506 decreases DDX39B protein levels by reducing the translational efficiency of DDX39B transcripts.

Gene-gene interaction between DDX39B and IL7R. Centered on the findings that the risk allele of rs2523506 reduces DDX39B protein level, and both the risk allele of IL7R rs6897932 and knockdown of DDX39B increased skipping of IL7R exon 6, the inventors postulated a functional relationship between rs6897932 in IL7R and rs2523506 in DDX39B. The inventors predicted that carriers of risk alleles in both genes (C in IL7R, and A in DDX39B) would exhibit higher risk of MS. The inventors therefore tested for evidence of multiplicative interaction (additive increase on the log odds scale) between rs2523506 and rs6897932 using logistic regression modeling. The interaction model included the main effects for rs2523506 and rs6897932, and was adjusted for population ancestry, cohort origin and all MEW risk variants outside the DDX39B locus (HLA-adjusted model) (see Table 3). There was a significant interaction between rs2523506 and rs6897932 (p=0.029), which was further investigated in rs6897932-stratified analyses with equivalent model adjustments. This approach revealed strong association between rs2523506 and rs6897932 with MS risk (Table 2, top). The inventors observed no elevated MS risk associated with DDX39B rs2523506 among individuals homozygous for the IL7R rs6897932 protective allele (TT, N=742, odds ratio (OR)=0.98, p=0.904), however an effect was observed among IL7R rs6897932 heterozygotes (CT, N=4251, OR=1.26, p=7.3×10$^{-4}$), and the magnitude and significance of the effect was strongest among individuals homozygous for the IL7R rs6897932 risk allele (CC, N=6239, OR=1.39, p=4.4×10$^{-9}$). When testing for the reciprocal relationship, that is the risk associated with IL7R rs6897932 in DDX39B rs2523506 stratified analyses (Table 2, middle), the inventors observed a subtle association of IL7R in non-carriers of the rs2523506 risk allele (CC, N=7834, OR=1.10, p=0.021), and this effect was drastically modified by the presence of the rs2523506 risk allele (AC, N=3099, OR=1.20, p=5.1×10$^{-3}$; AA, N=299, OR=2.19, p=7.5×10$^{-4}$). The inventors further determined the joint genotypic effect for all combinations of rs2523506 and rs6897932 genotypes (Table 2, bottom). This analysis uncovered a strong epistasis between these variants as the inventors observed increased MS risk only in carriers of at least one copy of the risk alleles at both loci (IL7R CT, DDX39B AC, N=1167, OR=1.32, p=0.023), and this effect was strongest in individuals homozygous for the risk allele at both loci (IL7R CC, DDX39B AA, N=156, OR=2.75, p=4.5×10$^{-7}$).

TABLE 2

Robust epistasis between risk alleles of IL7R rs6897932 and DDX39B rs2523506.

Association of rs2523506 and MS risk in individuals stratified by rs6897932 genotype

| | | IL7R rs6897932 | | | | | |
|---|---|---|---|---|---|---|---|
| | no | TT | | CT | | CC | |
| | strat. p-value | OR (95% CI) | p-value | OR (95% CI) | p-value | OR (95% CI) | p-value |
| DDX39B rs2523506 | 0.029 | 0.98 (0.70, 1.37) N = 742 | 0.904 | 1.26 (1.10, 1.45) N = 4251 | 7.3 × 10$^{-4}$ | 1.39 (1.25, 1.55) N = 6239 | 4.4 × 10$^{-9}$ |

Association of rs6897932 and MS risk in individuals stratified by rs2523506 genotype

| | | DDX39B rs2523506 | | | | | |
|---|---|---|---|---|---|---|---|
| | no | CC | | AC | | AA | |
| | strat. p-value | OR (95% CI) | p-value | OR (95% CI) | p-value | OR (95% CI) | p-value |
| IL7R rs6897932 | 0.029 | 1.10 (1.02, 1.20) N = 7834 | 0.021 | 1.20 (1.06, 1.37) N = 3099 | 5.1 × 10$^{-3}$ | 2.19 (1.39, 3.46) N = 299 | 7.5 × 10$^{-4}$ |

Joint genotypic effect of rs6897932 and rs2523506 on MS risk

| | | IL7R rs6897932 | | | | | |
|---|---|---|---|---|---|---|---|
| | | TT | | CT | | CC | |
| | | OR (95% CI) | p-value | OR (95% CI) | p-value | OR (95% CI) | p-value |
| DDX39B rs2523506 | CC | ref N = 498 | ref | 1.02 (0.82, 1.27) N = 2963 | 0.888 | 1.15 (0.93, 1.43) N = 4373 | 0.193 |
| | AC | 1.00 (0.69, 1.45) N = 322 | 0.986 | 1.32 (1.04, 1.69) N = 1167 | 0.023 | 1.53 (1.21, 1.92) N = 1710 | 3.2 × 10$^{-4}$ |
| | AA | 0.83 (0.29, 2.41) N = 22 | 0.738 | 1.36 (0.86, 2.15) N = 121 | 0.189 | 2.75 (1.86, 4.08) N = 156 | 4.5 × 10$^{-7}$ |

Interaction between rs2523506 and rs6897932 and association with MS risk was investigated using a logistic regression model adjusted for population stratification, cohort origin and HLA risk variants. The interaction model was further investigated using analyses stratified by rs6897932 (top) and rs2523506 (middle) genotypes. The bottom panel shows joint genotypic effect of rs6897932 and rs2523506 on MS risk. Bolded is the joint effect in homozygous carriers of the risk allele at both loci.

TABLE 3

Multivariable logistic meta-analysis identifies a significant multiplicative interaction between IL7R rs6897932 and DDX39B rs2523506 (Related to Table 2).

| Variable | | HLA model w/o interaction term | | | | HLA model with interaction term | | | |
|---|---|---|---|---|---|---|---|---|---|
| | | Beta | SE | OR | p-value | Beta | SE | OR | p-value |
| IL7R | | 0.138 | 0.035 | 1.15 | 8.90E−05 | 0.087 | 0.042 | 1.09 | 0.036 |
| DDX39B | | 0.269 | 0.042 | 1.31 | 1.70E−10 | 0.342 | 0.054 | 1.41 | 1.90E−10 |
| IL7R * DDX39B | | — | — | — | — | 0.144 | 0.066 | 1.16 | 0.029 |
| Intercept | | −0.826 | 0.063 | 0.44 | 1.20E−39 | −0.851 | 0.064 | 0.43 | 1.30E−40 |
| PC1 | | 3.762 | 0.936 | 43.03 | 5.90E−05 | 3.756 | 0.936 | 42.77 | 6.00E−05 |
| PC2 | | 9.689 | 0.958 | 16132.3 | 4.60E−24 | 9.721 | 0.958 | 16662.3 | 3.50E−24 |
| PC3 | | −1.418 | 0.926 | 0.24 | 0.126 | −1.403 | 0.927 | 0.25 | 0.13 |
| PC4 | | 2.565 | 0.915 | 12.99 | 5.10E−03 | 2.562 | 0.915 | 12.96 | 5.10E−03 |
| PC5 | | −4.695 | 0.924 | 0.01 | 3.70E−07 | −4.704 | 0.924 | 0.01 | 3.60E−07 |
| HLA-DRB1*15:01 | | 1.184 | 0.042 | 3.27 | 4.00E−174 | 1.184 | 0.042 | 3.27 | 3.00E−174 |
| HLA-DRB1*03:01 | | 0.281 | 0.047 | 1.32 | 2.40E−09 | 0.280 | 0.047 | 1.32 | 2.70E−09 |
| HLA-DRB1*13:01 | | −0.098 | 0.077 | 0.91 | 0.202 | −0.098 | 0.077 | 0.91 | 0.201 |
| HLA-DRB1*04:04 | | 0.275 | 0.100 | 1.32 | 5.70E−03 | 0.274 | 0.100 | 1.31 | 6.00E−03 |
| HLA-DRB1*04:01 | | −0.160 | 0.068 | 0.85 | 0.018 | −0.160 | 0.068 | 0.85 | 0.018 |
| HLA-DRB1*14:01 | | −0.509 | 0.160 | 0.60 | 1.50E−03 | −0.509 | 0.160 | 0.60 | 1.50E−03 |
| HLA-A*02:01 | | −0.329 | 0.037 | 0.72 | 1.30E−18 | −0.331 | 0.037 | 0.72 | 9.50E−19 |
| rs9277489 | | 0.275 | 0.035 | 1.32 | 9.60E−15 | 0.275 | 0.035 | 1.32 | 9.80E−15 |
| HLA-B*37:01 | | 0.538 | 0.114 | 1.71 | 2.10E−06 | 0.535 | 0.114 | 1.71 | 2.50E−06 |
| HLA-B*38:01 | | −0.540 | 0.154 | 0.58 | 4.70E−04 | −0.542 | 0.154 | 0.58 | 4.50E−04 |
| Cohort | ANZgene | ref | — | — | — | ref | — | — | — |
| | BWH/MIGEN | −0.882 | 0.056 | 0.41 | 1.20E−56 | −0.882 | 0.056 | 0.41 | 1.00E−56 |
| | IMSGC | −0.517 | 0.059 | 0.60 | 1.60E−18 | −0.517 | 0.059 | 0.60 | 1.60E−18 |
| | GeneMSA US | 0.464 | 0.083 | 1.59 | 2.80E−08 | 0.465 | 0.084 | 1.59 | 2.50E−08 |
| | GeneMSA Netherlands | 0.266 | 0.111 | 1.30 | 0.016 | 0.268 | 0.111 | 1.31 | 0.016 |
| | GeneMSA Switzerland | 0.568 | 0.113 | 1.77 | 4.80E−07 | 0.571 | 0.113 | 1.77 | 4.30E−07 |
| Number of observations | | 11232 | | | | 11232 | | | |
| Log likelihood | | −6371.5059 | | | | −6369.0997 | | | |
| LR chi1 (df) | | 1985.80 (22) | | | | 1990.61 (23) | | | |
| Prob > chi2 | | <0.00005 | | | | <0.00005 | | | |
| Pseudo R2 | | 0.1348 | | | | 0.1352 | | | |

Multivariable logistic regression meta-analyses demonstrate evidence for a significant multiplicative interaction between IL7R rs6897932 and DDX39B rs2523506, adjusted for population substructure, known HLA risk variants, and cohort of origin. The table illustrates the output for each adjusted variable with comparison between the two models: the HLA adjusted model without (left) and with (right) the interaction term between IL7R rs6897932 and DDX39B rs2523506 (bolded parameters) [Beta=beta coefficient; SE=standard error; OR=odds ratio]. Both models are stable and model parameters are consistent, with the exception of the significant statistical interaction.

It should be noted that interaction between DDX39B and IL7R was not due to an interaction between IL7R and HLA-DRB1*15:01, the main genetic driver of MS (International Multiple Sclerosis Genetics et al., 2015; Patsopoulos et al., 2013), as the inventors observed no evidence for a multiplicative interaction between rs6897932 and HLA-DRB1*15:01 with MS risk (Table 4). Taken together, the inventors concluded that the risk alleles in DDX39B and IL7R show strong evidence of epistasis, with a robust dose-dependent effect, suggesting that the MS risk associated with low levels of DDX39B can be explained by its action on IL7R.

TABLE 4

Lack of evidence for a multiplicative interaction between risk alleles of IL7R rs6897932 and HLA-DRB1*15:01 (Related to Table 2).

| | | IL7R rs6897932 | | | | | |
|---|---|---|---|---|---|---|---|
| | | TT | | CT | | CC | |
| | no strat. p-value | OR (95% CI) | p-value | OR (95% CI) | p-value | OR (95% CI) | p-value |
| HLA-DRB1*15:01 | 0.11 | 3.75 (2.69, 5.22) | $6.5 \times 10^{-15}$ | 3.50 (3.05, 4.02) | $3.2 \times 10^{-71}$ | 3.11 (2.78, 3.46) | $4.4 \times 10^{-92}$ |

The inventors tested for evidence of interaction between HLA-DRB1*15:01 and rs6897932 using a logistic regression model adjusted for population stratification, cohort origin and HLA risk variants, including the DDX39B rs2523506 variant (Table 2); results were not significant (no strat.). Stratification of individuals by rs6897932 genotypes (IL7R-TT (N=742), CT (N=4251) and CC (N=6239)) for analysis of DRB1*15:01 revealed strong association with MS across all three strata (note the overlap in 95% confidence intervals). The results indicate the interaction between DDX39B and IL7R is not due to an interaction between IL7R and HLA-DRB1*15:01, and thus, it is likely that this interaction between DDX39B and IL7R could explain part of the heretofore unaccounted heritable risk of MS.

Figure 5:
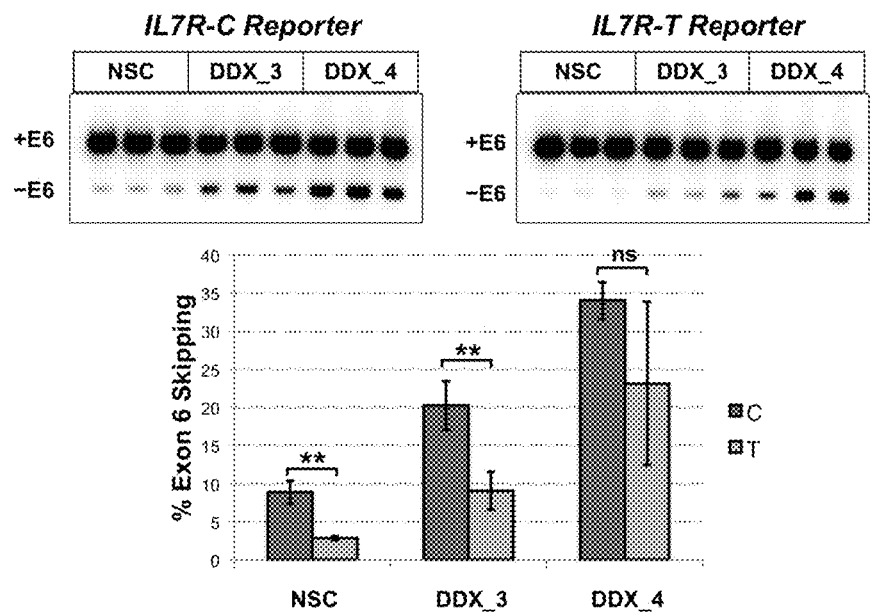
FIG. 5 shows the functional interaction between DDX39B and IL7R exon 6 variants. The interaction between DDX39B and IL7R was functionally tested in DDX39B-depleted HeLa cells using IL7R splicing reporters carrying either the risk C allele (IL7R-C; left) or the protective T allele (IL7R-T; right) of rs6897932. RT-PCR analysis of exon 6 splicing (mean±s.d.) reveals higher exon 6 skipping when the levels of DDX39B are reduced in the context of the risk C allele than of the protective T allele of rs6897932 (Student's t-test, two-sided; ** $p \leq 0.005$).

The epistasis between DDX39B rs2523506 and IL7R rs6897932 suggested the possibility of a functional interplay that could enhance skipping of IL7R exon 6 in carriers of the risk alleles at both loci. Indeed, knockdown of DDX39B revealed higher skipping of exon 6 in transcripts from a reporter carrying the risk allele of rs6897932 (IL7R-C) compared to the protective allele (IL7R-T) (FIG. 5). This result is consistent with exon 6 skipping being augmented by two insults: strengthening of a weak silencer by the risk allele of rs6897932 (Evsyukova et al., 2013; Gregory et al., 2007) and reduced expression of the activator DDX39B. Collectively, the genetic and functional studies indicate that carriers of both IL7R and DDX39B risk alleles are at highest risk of developing MS, very likely due to increased expression of sIL7R.

Figure 6A:
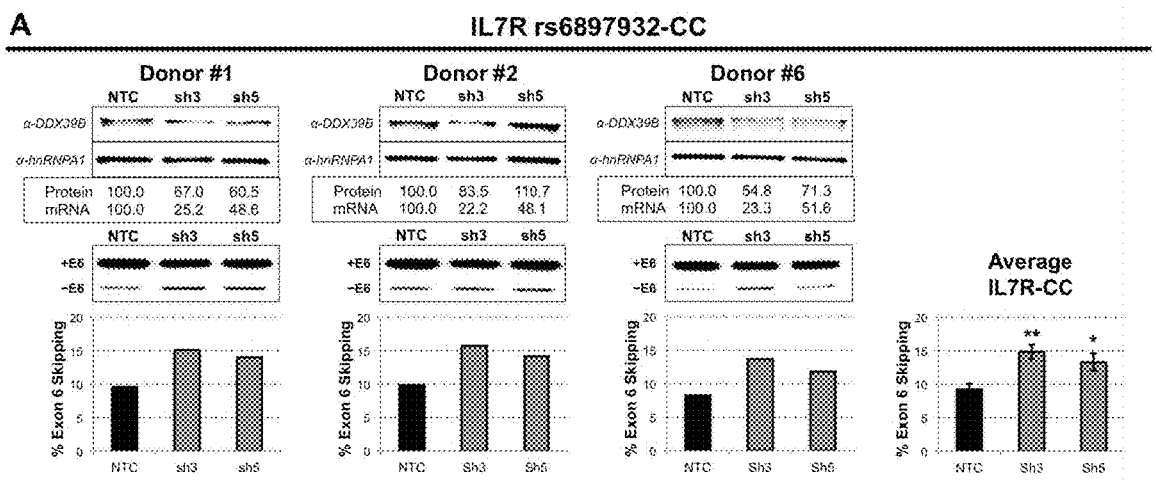
FIGS. 6A and 6B show that DDX39B controls alternative splicing of IL7R exon 6 in primary $CD4^+$ T cells. Knockdown of DDX39B in primary $CD4^+$ T cells from six donors via lentiviral transduction with two independent shRNA against DDX39B (sh3 and sh5) and a non-targeting control shRNA (NTC). Donors are grouped by IL7R genotype: IL7R-CC (FIG. 6A) and IL7R-CT (FIG. 6B), and each panel illustrates DDX39B western blot analysis (top) and RT-PCR analysis of IL7R exon 6 splicing (bottom) for each donor individually. In each panel, the plots on the right show the average of % exon 6 skipping for each IL7R genotype (mean±s.d., Student's t-test: ** $p \leq 0.005$; * $p \leq 0.05$).
Figure 6B:
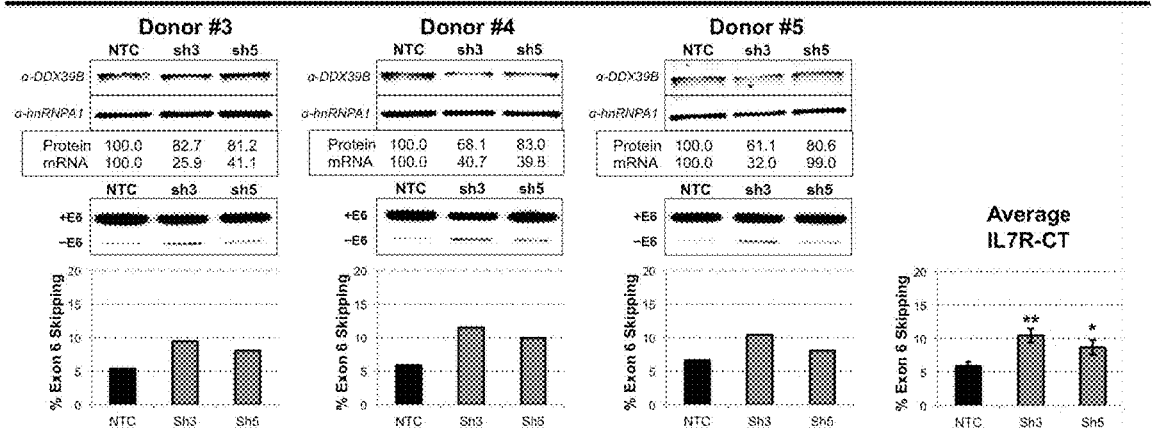

DDX39B regulates IL7R exon 6 inclusion in primary CD4+ T cells. The inventors then explored the effect of DDX39B knockdown on IL7R exon 6 splicing in CD4+ T cells isolated from healthy human donors who were either CC (FIG. 6A) or CT (FIG. 6B) at rs6897932 in IL7R. The inventors transduced cells from six donors with lentiviruses expressing two independent shRNAs against DDX39B or a non-targeting control shRNA. Even though DDX39B knockdown was less efficient in primary CD4+ T cells than in HeLa cells, the inventors observed similar increase in exon 6 skipping upon DDX39B depletion (FIGS. 6A and 6B). The inventors also measured sIL7R levels by ELISA and found increased levels of sIL7R upon DDX39B knockdown in cells from all donors with one DDX39B shRNA (sh3) but only in cells from two donors with the second shRNA (sh5). While the lack of correlation of sIL7R levels with exon 6 skipping in cells transduced with sh5 remains unexplained, the inventors note it could be due to the fact that the antibody used can detect all IL7R protein isoforms. Importantly, the inventors observed higher levels of exon 6 skipping upon DDX39B depletion in CD4+ T cells from donors homozygous for the risk allele in IL7R (CC) than those from heterozygous (CT) (FIGS. 6A and 6B), corroborating the results obtained with the IL7R splicing reporters (FIG. 5). These data are consistent with the observed DDX39B-IL7R epistasis above (Table 2). The inventors concluded DDX39B plays an important role in promoting IL7R exon 6 inclusion in primary CD4+ T cells, thereby underscoring the importance of DDX39B in MS pathogenesis.

The inventors previously showed that the cis-acting rs6897932 C allele in exon 6 of IL7R, which is strongly associated with MS susceptibility, increases skipping of exon 6 (Evsyukova et al., 2013; Gregory et al., 2007), and this correlates with elevated levels of circulating sIL7R (Hoe et al., 2010; Lundstrom et al., 2013). This is predicted to have important repercussions on the pathogenesis of MS as sIL7R has been shown to exacerbate the severity of EAE, a mouse model of MS (Lundstrom et al., 2013). The inventors have now found that trans-acting factors controlling exon 6 splicing are indicative of MS susceptibility. Using a multi-disciplinary approach consisting of biochemical, molecular genetic, and human genetic investigations, the inventors show herein that the RNA helicase DDX39B is: (1) a potent trans-activator of IL7R exon 6 in cell lines and primary human CD4+ T cells, (2) a repressor of sIL7R, and (3) a novel risk factor for MS. Of the numerous DDX39B variants found to be strongly associated with MS risk, the inventors identified rs2523506 as a putative functional variant that exhibits strong correlation with reduced DDX39B protein expression in LCLs. Indeed, functional studies with luciferase reporters showed that the risk allele of this 5' UTR variant diminishes the translational efficiency mediated by DDX39B 5' UTRs, thereby directly linking the SNP to the observed changes in protein levels. Additionally, rs2523506 does not affect expression of nearby genes, including pro-inflammatory cytokines of the tumor necrosis factor superfamily (TNF, LTA and LTB). These findings suggest that increased MS risk associated with DDX39B could largely result from its function on IL7R splicing.

DDX39B is a DEAD-box protein with known functions in constitutive pre-mRNA splicing (Shen et al., 2008; Shen et al., 2007) and nuclear export of mRNAs (Luo et al., 2001; Masuda et al., 2005; Strasser et al., 2002). The increased skipping of exon 6 observed upon DDX39B knockdown may result from other functions of DDX39B, in particular mRNA nuclear export. This is unlikely, however, as the inventors have previously shown that the effects of rs6897932 and ESE2 are recapitulated in in vitro splicing assays with HeLa nuclear extracts (Evsyukova et al., 2013), which implies a direct effect on exon 6 splicing rather than nuclear export. Moreover, the role of DDX39B in promoting exon 6 inclusion appears to be independent of its function in constitutive pre-mRNA splicing, wherein DDX39B facilitates recruitment of U2 snRNP to the branchpoint through its interaction with U2AF65. Here, the inventors showed that DDX39B requires an intact ESE2 to promote inclusion of exon 6, as functionally supported by failure to pull-down DDX39B with ΔESE2 exon 6 RNAs, and the inability of DDX39B to affect exon 6 inclusion in the absence of ESE2. Based on these results, the inventors propose that DDX39B binds to ESE2, directly or indirectly, to promote inclusion of IL7R exon 6, and by doing so it decreases sIL7R expression and reduces MS risk.

Using powerful genetic association analyses that interrogated candidate trans-acting factors identified in the proteomic screen, the inventors uncovered DDX39B as the lone candidate trans-factor exhibiting strong association with MS risk independently of HLA risk variants. Interestingly, none of the associated variants in the HLA-adjusted model had an effect before correction for HLA risk factors, suggesting masking by HLA associations. A similar phenomenon was previously reported for rs2516489, a variant located in an intergenic region within 10 kb of DDX39B, which showed association only after adjusting for other HLA risk variants (Patsopoulos et al., 2013). The authors proposed Simpson's paradox as a likely explanation, wherein HLA and DDX39B variants are associated independently but the effect of DDX39B variants is likely masked by the effects of HLA variants. This masking by HLA variants may explain why associations of DDX39B with autoimmune diseases have not been as prominent as the inventors would expect. Importantly, the inventors observed dramatic allele-specific variation of DDX39B protein levels (up to two-fold) due to rs2523506 genotype among LCLs of African origin, and to a lesser extent among LCLs of European origin, which mainly results from an effect of rs2523506 on translational efficiency. A perplexing result is the stronger correlation of rs2523506 genotype with DDX39B protein levels in African than in European LCLs. While a complete explanation of this finding is not yet at hand, the data indicate that regulation of DDX39B levels is likely complex, and other genetic or epigenetic modifiers could titer DDX39B expression or activity. Nonetheless, it is remarkable that the correlation between DDX39B protein levels and rs2523506 genotype was observed by two distinct experimental methods, namely western blot (this work) and mass spectrometry (Wu et al., 2013), and in two populations of LCLs (YRI/ESN and IBS).

An important finding in this study is the epistatic interaction between rs2523506 in DDX39B and rs6897932 in IL7R. This interaction was missed in a recent study that investigated potential polygenic interactions in MS between HLA risk alleles and established non-HLA MS risk variants, including IL7R, because non-HLA risk variants within the MHC, such as rs2516489 and rs2523506, were not interrogated (International Multiple Sclerosis Genetics et al., 2015). It has been long thought that functional polymorphisms affecting genes within the same gene network could enhance disease risk in complex genetic disorders but this has been difficult to prove. For instance, several studies have reported suggestive evidence for genetic interactions in several autoimmune diseases including Systemic Lupus Erythematosus (Zhou et al., 2012), Rheumatoid Arthritis (Briggs et al., 2010; Perdigones et al., 2010) and MS (Shahbazi et al., 2011). Nonetheless, all these cases lack functional validation and understanding of the underlying molecular mechanisms. Here, the inventors demonstrated that the epistasis between DDX39B rs2523506 and IL7R rs6897932 confers higher susceptibility to MS in a dose-dependent manner. More importantly, the inventors functionally demonstrated that the risk alleles at both loci work in concert to increase skipping of IL7R exon 6, thereby enhancing the biogenesis of sIL7R. This study represents a rare example where the molecular underpinnings of a pathogenic epistatic interaction are understood and have been functionally validated.

Lastly, these studies demonstrate a protective role for DDX39B in the pathogenesis of MS, wherein decreased DDX39B expression results in up-regulation of sIL7R via skipping of IL7R exon 6. Although the multidisciplinary study centers on MS, other genetic studies have suggested associations of variants within DDX39B with other autoimmune diseases including Rheumatoid Arthritis (Kilding et al., 2004; Okamoto et al., 2003; Quinones-Lombrana et al., 2008), Type 1 Diabetes (Barrett et al., 2009; Cheong et al., 2001; Price et al., 2004; Wong et al., 2003) and Atopic Dermatitis (Paternoster et al., 2012); therefore, it is likely that DDX39B play a similar protective role in these diseases. This is supported by findings of elevated plasma levels of sIL7R in patients of Rheumatoid Arthritis (Badot et al., 2011), Type 1 Diabetes (Monti et al., 2013), and Systemic Lupus Erythematosus (Lauwerys et al., 2014). In addition, DDX39B has also been proposed to negatively regulate production of pro-inflammatory cytokines TNFα, IL1, and IL6 (Allcock et al., 2001). Collectively, these data imply that DDX39B may play a larger role than previously appreciated in the regulation of immune function and in the development of autoimmunity.

TABLE 5

Oligonucleotide primers used in this study.

| SEQ ID NO: | Primer description | Primer sequence |
|---|---|---|
| 1 | DDX39B cloning start codon | AAGCTTGCCACCATGGC AGAGAACGATGTGGACA ATGAG |
| 2 | DDX39B cloning stop codon | CTCGAGCTACCGTGTCT GTTCAATGTAGGAGGA |
| 3 | T7 forward (splicing) | TAATACGACTCACTATA GGGAGA |
| 4 | SP6 reverse (splicing) | ATTTAGGTGACACTATA GAA |
| 5 | IL7R exon 5 forward (splicing) | GGCAGCAATGTATGAGA TTAAAGTTCG |
| 6 | IL7R exon 7 reverse (splicing) | CAAAGATGTTCCAGAGT CTTCTTATGATC |
| 7 | IL7R exon 3 forward RT-qPCR | CAATATATGTGTGAAGG TTGGAGAA |
| 8 | IL7R exon 4 reverse RT-qPCR | CATTGGCTCCTTCCCGA TAG |
| 9 | GAPDH forward RT-qPCR | AGCCACATCGCTCAGAC AC |
| 10 | GAPDH reverse RT-qPCR | GCCCAATACGACCAAAT CC |
| 11 | DDX39B exon 6 forward RT-qPCR | GTGCTACCTTGAGCAAA GAGA |
| 12 | DDX39B exon 7 reverse RT-qPCR | AACCCATGCAGCGTCAA |
| 13 | DDX5 exon 13 forward RT-qPCR | AGCAAGTGAGCGACCTT ATC |
| 14 | DDX5 exon 14 reverse RT-qPCR | CATCCTTCATGCCTCCT CTAC |
| 15 | DDX17 exon 12 forward RT-qPCR | AGGCCAATCAGGCTATC AATC |
| 16 | DDX17 exon 13 reverse RT-qPCR | CTGAAGAAGTGGTCCGG TAAC |
| 17 | DDX23 exon 16 forward RT-qPCR | TCCAAGATGTGTCTATG GTTGTC |
| 18 | DDX23 exon 17 reverse RT-qPCR | GAACACAGCAGAGTCCT CTTT |
| 19 | MICB exon 4 forward RT-qPCR | ATGGAACACAGCGGGAA T |
| 20 | MICB exon 5 reverse RT-qPCR | CATGGCATAGCAGCAGA AAC |
| 21 | MCCD1 exon 1 forward RT-qPCR | CAAAGCAAGCATGGAAG AGC |
| 22 | MCCD1 exon 2 reverse RT-qPCR | CTGCTGCTCCAACAACT CT |
| 23 | ATP6V1G2 exon 3 forward RT-qPCR | AGCTTCTTGGCATGGTC TG |
| 24 | ATP6V1G2 exon 3 reverse RT-qPCR | GATTTCTTTGAGGGAGG GAACT |
| 25 | NFKBIL1 exon 2 forward RT-qPCR | GGGACACGGCACTGCAT |

TABLE 5-continued

Oligonucleotide primers used in this study.

| SEQ ID NO: | Primer description | Primer sequence |
|---|---|---|
| 26 | NFKBIL1 exon 3 reverse RT-qPCR | GGAGGGACAGCGGCTTA |
| 27 | LTA exon 3 forward RT-qPCR | CAAACCTGCTGCTCACCT |
| 28 | LTA exon 4 reverse RT-qPCR | GGGACCAGGAGAGAATTGTTG |
| 29 | TNF exon 3 forward RT-qPCR | CAAGCCTGTAGCCCATGTT |
| 30 | TNF exon 4 reverse RT-qPCR | GAGGTACAGGCCCTCTGAT |
| 31 | LTB exon 3 forward RT-qPCR | GGAGCCAGAAACAGATCTCAG |
| 32 | LTB exon 4 reverse RT-qPCR | CTCGTCAGAAACGCCTGTT |
| 33 | R-Luc ORF forward RT-qPCR | CAGTGGTGGGCCAGATGTAAACAA |
| 34 | R-Luc ORF reverse RT-qPCR | TAAGAAGAGGCCGCGTTACCATGT |
| 35 | F-Luc ORF forward RT-qPCR | CGGAAAGACGATGACGGAAA |
| 36 | F-Luc ORF reverse RT-qPCR | CGGTACTTCGTCCACAAACA |

TABLE 6 siRNAs used in this study.

| Number | Gene | siRNA description | Source | Catalog number |
|---|---|---|---|---|
| 1 | Non-silencing control | NSC [All Stars Non-silencing control] | Qiagen | SI03650318 |
| 2 | DDX39B | DDX_3 [Hs_BAT1_11] | Qiagen | SI04368147 |
| 3 | DDX39B | DDX_4 [Hs_BAT1_13] | Qiagen | SI05107942 |
| 4 | DDX5 | DDX5_1 [Hs_DDX5_10] | Qiagen | SI04178293 |
| 5 | DDX5 | DDX5_2 [Hs_DDX5_11] | Qiagen | SI04228917 |
| 6 | DDX5 | DDX5_3 [Hs_DDX5_13] | Qiagen | SI04294486 |
| 7 | DDX17 | DDX17_1 [Hs_DDX17_4] | Qiagen | SI00361018 |
| 8 | DDX17 | DDX17_2 [Hs_DDX17_5] | Qiagen | SI03197033 |
| 9 | DDX17 | DDX17_3 [Hs_DDX17_7] | Qiagen | SI04223198 |
| 10 | DDX23 | DDX23_1 [Hs_DDX23_6] | Qiagen | SI03144743 |
| 11 | DDX23 | DDX23_2 [Hs_DDX23_7] | Qiagen | SI04190326 |
| 12 | DDX23 | DDX23_3 [Hs_DDX23_8] | Qiagen | SI04204767 |
| 13 | MICB | MICB_1 [Hs_MICB_2] | Qiagen | SI00082796 |
| 14 | MICB | MICB_2 [Hs_MICB_6] | Qiagen | SI02636298 |
| 15 | MICB | MICB_3 [Hs_MICB_7] | Qiagen | SI03083031 |
| 16 | NFKBIL1 | NFKBIL1_1 [Hs_NFKBIL1_6] | Qiagen | SI03239761 |
| 17 | NFKBIL1 | NFKBIL1_2 [Hs_NFKBIL1_7] | Qiagen | SI04231234 |
| 18 | NFKBIL1 | NFKBIL1_3 [Hs_NFKBIL1_8] | Qiagen | SI04256539 |
| 19 | LTA | LTA_1 = Hs_LTA_1 | Qiagen | SI00012467 |
| 20 | LTA | LTA_2 = Hs_LTA_5 | Qiagen | SI03024994 |
| 21 | LTA | LTA_3 = Hs_LTA_6 | Qiagen | SI03073203 |
| 22 | TNF | TNF_1 = Hs_TNF_1 | Qiagen | SI00012439 |
| 23 | TNF | TNF_2 = Hs_TNF_2 | Qiagen | SI00012446 |

Cell lines and culture conditions. HeLa and Jurkat T cells were obtained from the Duke University Cell Culture Facility. This facility provides authenticated cell lines free of mycoplasma contamination. HeLa Flp-In T-Rex cell line (Kaiser et al., 2008) was kindly provided by Dr. E Dobrikova (Duke University). LCLs were obtained from the Coriell Institute Cell Repositories. HeLa cells were grown in DMEM medium (Life Technologies), whereas Jurkat T cells and LCLs were grown in Advanced 1640 RPMI medium (Life Technologies); both medium were supplemented with 10% heat-inactivated FBS (Gemini Bio-Products) and 1% antibiotics (Pen Strep; Life Technologies).

Primary human $CD4^+$ T cells collection and culture. Informed consent was obtained from healthy volunteers for blood donation. Collection of blood samples was in accordance with the research protocol entitled "Characterizing human immune response signatures that predict clinical outcomes by isolating PBMCs, serum and plasma from normal donors which will be used for optimization, validation and serve as normal controls for immune profiling assays" (Protocol ID: Pro00070584, Kent Weinhold, PI) approved by the Institution Review Board at Duke University. Peripheral blood mononucleated cells (PBMCs) were extracted from whole blood using the Ficoll method and $CD4^+$ T cells were further isolated using $CD4^+$ T cell isolation kit (Miltenyi Biotec). Isolated primary $CD4^+$ T cells were cultured in Advanced 1640 RPMI medium supplemented with 20% heat-inactivated FBS, 1% antibiotics and 100 ng/mL human recombinant IL-2 (Peprotech). 48 hours prior transduction, $CD4^+$ T cells were activated with anti-CD3 (50 ng/mL; eBioscience) and anti-CD28 (100 ng/mL; BD Biosciences) antibodies in the media.

DNA and RNA collection from human PBMC and LCL. Informed consent was obtained from RRMS patients and healthy volunteers enrolled in the MURDOCK-MS study. Blood samples were drawn from these individuals for DNA and RNA isolation. Sample collection was in accordance with the research protocol associated with this study as approved by the Institution Review Board at Duke University. Genomic DNA and total RNA were isolated from whole blood using the QIAamp DNA Blood mini kit (QIAGEN) and PAXgene Blood RNA kit (QIAGEN), respectively. The inventors point out that although these RNA samples were isolated from whole blood, throughout the text the inventors referred to them as isolated from PBMCs, given that the majority of nucleated cells in whole blood are PBMCs. Additional samples from individuals enrolled at Duke University were isolated from PBMCs using Trizol reagent. For LCLs, total RNA was harvested using the ReliaPrep RNA Cell Miniprep System (Promega). All RNA samples were treated with TURBO DNase (Ambion) according to the manufacturer's protocol.

Generation of stable cell line expressing DDX39B. HeLa cells stably expressing an inducible DDX39B cDNA trans-gene were generated using the Flp-In T-Rex system (Life Technologies) as recommended by the manufacturer. HeLa Flp-In T-Rex cell line (Kaiser et al., 2008) was kindly provided to the group by Dr. E Dobrikova (Duke University). The coding sequence of DDX39B was amplified with Phusion High-Fidelity DNA polymerase (New England BioLabs) using as template cDNA prepared from total RNA isolated from human PBMCs. Forward and reverse primers contained HindIII and XhoI restriction sites, respectively. The resulting PCR amplicon was cloned into pcDNA5/FRT/TO plasmid using HindIII and XhoI restriction sites and verified by Sanger sequencing. This plasmid was co-transfected with pOG44 plasmid, which encodes the Flp recombinase, into HeLa Flp-In T-Rex cells using Lipofectamine 2000 (Life Technologies) according to the manufacturer's instructions. Transfected cells were grown in DMEM medium supplemented with 10% FBS free of tetracycline (GE Healthcare Life Sciences) under blasticidin/hygromycinB selection for 15 days, and resistant cells were expanded and used for subsequent experiments. Expression of the trans-gene was induced by addition of tetracycline at 50 μg/ml.

Genotyping of human primary cells and LCLs. DNA samples from human PBMCs and primary $CD4^+$ T cells were genotyped for DDX39B rs2523506 and IL7R rs6897932 using TaqMan genotyping assays (Applied Biosystems) or by sequencing. LCLs were previously genotyped in the HapMap project (International HapMap, 2003, 2005; International HapMap et al., 2007).

Transfection of IL7R splicing reporters. IL7R reporter minigenes, previously described in (Gregory et al., 2007), consisted of the genomic region of IL7R encompassing 614 bp of intron 5, exon 6 and 573 bp of intron 6, cloned in between constitutive upstream (U) and downstream (D) exons in the pI-11 plasmid. Three versions of the IL7R reporter minigene were used containing the alternative alleles of rs6897932 (C or T) or mutation of ESE2 in the context of the risk C allele (ΔESE2). These IL7R splicing reporters (25 ng per well in 24-well format) were transfected into HeLa cells or Jurkat T cells using Lipofectamine 2000 or FuGENE 6 (Roche), respectively, according to the manufacturer's recommendations. Total RNA was harvested 48 hours after transfection using Trizol Reagent (Life Technologies). Exon 6 skipping was determined for each reporter by RT-PCR as delineated below.

DDX39B RNAi-mediated knockdown and rescue. siRNA duplexes against DDX39B were purchased from Qiagen (DDX_3=Hs BAT1_11; DDX_4=Hs BAT1_13) and diluted to a final concentration of 10 μM upon arrival. Two independent siRNAs were used to account for potential off-target effects. AllStars Negative Control siRNA (Qiagen) was used as negative control in all knockdown experiments. Transfections were performed in biological triplicates for each siRNA. 24 hours prior to siRNA transfection, $5 \times 10^4$ HeLa cells were seeded in 500 μL of DMEM medium per well in 24-well plate format. siRNAs were diluted in Opti-MEM I medium (Life Technologies) and transfected at final concentration of 50 nM on days 1 and 3 post-seeding using Lipofectamine RNAiMax (Life Technologies), following the manufacturer's recommendations. On day 5 post-seeding, the cells were transfected with 25 ng of the corresponding IL7R reporter minigene using Lipofectamine 2000 (Life Technologies) under the manufacturer's recommendations. Two versions of the IL7R reporter minigene were used containing the alternative alleles of rs6897932 (IL7R-C and IL7R-T): for the experiments in FIGS. 1A to 1F the inventors used the IL7R-C reporter, whereas for the experiments in FIG. 5 the inventors used both IL7R-C and IL7R-T reporters. On day 7, cells were harvested with Trizol Reagent (Life Technologies) or ReliaPrep RNA Cell Miniprep System (Promega) for RNA isolation, or with 1×RIPA buffer for protein extraction. DDX39B depletion was determined by western blotting as delineated below. Percentage IL7R exon 6 skipping was determined by RT-PCR (see section RT-PCR analysis of IL7R splicing). Knockdown experiments were performed three times with similar results.

For the rescue experiment in FIGS. 1A to 1F, HeLa cells stably expressing a DDX39B cDNA trans-gene, either wild type (wt) or a helicase mutant (D199A, previously characterized in (Shen et al., 2008; Shen et al., 2007)), were grown in the absence or the presence of tetracycline to control expression of the trans-gene. Cells were transfected with the corresponding siRNAs on days 1, 3 and 5 post-seeding. For this experiment the inventors used DDX39B siRNA DDX_4 because it targets the 3' UTR of the endogenous DDX39B transcripts, which is not present in transcripts from the cDNA trans-genes. Cells were harvested on day 9 with the ReliaPrep RNA Cell Miniprep System (Promega) for RNA isolation or with 1×RIPA buffer for western blot analysis. These experiments were performed at least two times with similar results. For the experiment with IL7R-ΔESE2 splicing reporter, this reporter was transfected into cells on day 7 and cells were harvested on day 9 as above.

In both knockdown and rescue experiments the relative level of DDX39B protein was verified by western blotting. Total protein was harvested using 1×RIPA buffer (150 mM NaCl, 1% NP-40, 0.5% sodium deoxycholate, 0.1% SDS, and 50 mM Tris-HCl at pH 7.5) freshly supplemented with 1× protease inhibitors (Roche). 10 μg of total protein were loaded per lane on NuPAGE 4%-12% Bis-Tris pre-cast gels (Life Technologies), transferred to nitrocellulose membranes (Whatman), and blotted using standard protocols with anti-DDX39B rabbit polyclonal antibody (Abcam, ab47955) and anti-hnRNPA1 mouse monoclonal antibody (Abcam, ab5832) as loading control.

RNAi-mediated knockdown of other genes products. Knockdown of RNA helicases DDX5, DDX17 and DDX23, and of genes in the vicinity of the DDX39B locus (MICB, NFKBIL1, LTA and TNF) were performed in HeLa cells with at least two independent siRNAs and the non-silencing control siRNA (NSC). Three additional genes in this region (MCCD1, ATP6V1G2 and LTB) are not expressed in HeLa cells and thus were not tested. siRNA transfections were carried out as before but at a final siRNA concentration of 30 nM. Cells were harvested on day 5 post-seeding for RNA isolation using the ReliaPrep RNA Cell Miniprep System. Knockdown levels were quantified by RT-qPCR and normalized to GAPDH as detailed below. IL7R exon 6 skipping was determined by RT-PCR as delineated below. These experiments were performed once in biological triplicates.

Lentiviral packaging. DDX39B shRNA pLKO.1 vector (sh3=TRCN0000286976; sh5=TRCN0000294383) and the Mission non-targeting control shRNA pLKO.1 vector (SHC002) were purchased from Sigma-Aldrich. Lentiviral packaging of these shRNA constructs was carried out in 293T cells using Polyethylenimine (PEI) method. In brief, $7.5 \times 10^6$ cells were seeded in 15-cm dishes in DMEM media supplemented with 10% FBS and 1% antibiotics 24 hours prior transfection (3 15-cm dishes per construct). Cells were co-transfected with 17 µg of the corresponding shRNA pLKO.1 vectors or GFP control vector (pLCE), 17 µg of packaging plasmid (pCMVR8.74) and 7 µg of VSV-G envelope plasmid (pMD2.G) in serum-free media and 120 µg PEI. DNA-PEI mixes were added drop-wise to the corresponding dishes and 18 hours after the medium was replaced with 20 mL fresh DMEM media. After 72 hours, supernatants were collected, filtered through 0.45 µm filters and concentrated to 6 mL in Amicon Ultra 100K centrifugal filter units (EMD Millipore). Concentrated lentiviral particles were stored at 4° C. overnight.

Transduction of primary human CD4+ T cells. Primary CD4+ T cells from 6 different donors were transduced following modifications to the method in (Bilal et al., 2015). In brief, $4.0 \times 10^6$ activated primary CD4+ T cells from each donor were transduced with 1 mL of the corresponding concentrated lentivirus in the presence of 8 µg/mL hexadimethrine bromide (Sigma-Aldrich) at a final density of $1.0 \times 10^6$ cells/mL in RPMI media supplemented with 20% FBS, 1% antibiotics and 100 ng/mL recombinant human IL-2. Transductions were carried out for 72 hours, followed by antibiotic selection with puromycin (1.5 µg/mL) for 96 hours. Prior to the start of puromycin selection, GFP-transduced cells were assayed for GFP expression by flow cytometry. Cells were transduced at 50-60% efficiency as determined by % GFP positive cells, and were enriched to >90% by puromycin selection. 24 hours prior to collection, cells were resuspended in RPMI media without puromycin and IL-2 for analysis. Supernatants were collected for quantification of sIL7R secretion, and cells were harvested for RNA isolation with the ReliaPrep RNA Cell Miniprep System (Promega) or for protein extraction with 1×RIPA buffer as before. Knockdown of DDX39B was determined by western blotting as before, and by RT-qPCR with normalization to GAPDH. IL7R exon 6 skipping and sIL7R secretion were quantified by RT-PCR and ELISA, respectively, as described below.

RT-PCR analyses of IL7R splicing. Total RNA was harvested using either Trizol Reagent (Life Technologies) or the ReliaPrep RNA Cell Miniprep System (Promega) according to the manufacturer's instructions. Isolated RNAs were treated with TURBO DNase (Ambion) or DNase I (Promega) to degrade contaminating DNA following the company's recommendations. 0.2-1.0 µg of DNase-treated total RNA was used as template for reverse transcription using either the ImProm-II Reverse Transcription System (Promega) or the High Capacity cDNA Reverse Transcription System (Applied Biosystems) and random hexamer primers. PCR reactions were prepared as follows: 5 µL of the corresponding RT reaction (diluted 1:5) was mixed with 200 nM of forward and reverse primers (see below), 100 nM dNTPs, 50 mM KCl, 2 mM $MgCl_2$, 0.3 µL of Taq polymerase, and [$\alpha$-$^{32}$P]dCTP (3000 Ci/mmol, 10 mCi/mL, PerkinElmer) at a final concentration of 0.1 µCi/µL. PCR primers for minigene constructs (IL7R-C, IL7R-T and IL7R-ΔESE2) were complementary to T7 (forward) and SP6 (reverse) promoter sequences present in the construct, respectively (Gregory et al., 2007). PCR primers for endogenous IL7R were complementary to exon 5 (forward) and exon 7 (reverse). PCR products were electrophoresed on 6% non-denaturing polyacrylamide/TBE gels, dried in a gel drier and exposed to a Molecular Dynamics Phosphorimager screen. Quantifications were performed using ImageQuant software (Molecular Dynamics). Percentage exon 6 skipping was determined as: [(skipped product)/(included+skipped products)×100]. The data are presented as the mean of triplicate samples and error bars represent standard deviations. Statistical significance in knockdown and rescue studies was assessed using Student's t-test (two-sided).

Quantification of sIL7R by ELISA. Supernatants from the DDX39B knockdown experiments in HeLa cells and primary CD4+ T cells described above were collected and concentrated to 100 µl by centrifugation in Amicon Ultra 3K centrifugal filters (Millipore, UFC500324). Secreted sIL7R was quantified from the concentrated supernatants by ELISA as in (Crawley et al., 2010). In brief, 96-wells plate (R&D Systems, DY990) were coated at 4° C. overnight with a mouse anti-human IL7R monoclonal antibody (R&D Systems, MAB306). The next day, the plates were blocked with 3% BSA in PBS for one hour (room temp), followed by two-hour incubation (room temp) with the concentrated supernatants, and four washes with PBS-Tween (0.05%). Detection of bound sIL7R was carried out by one-hour incubation (room temp) with biotinylated goat anti-human IL7R polyclonal antibody (R&D Systems, BAF306), followed by 30-minute incubation (room temp) with streptavidin-horseradish peroxidase (Millipore, #18-152), and 20-minute incubation (room temp) with TMB peroxidase substrate (SurModics BioFX, TMBW-1000-01), with four washes with PBS-Tween (0.05%) between manipulations. The reaction was stopped with 1N $H_2SO_4$, and the product was visualized in a plate reader at 450 nm. The concentration of samples was extrapolated from standard curves of recombinant human IL7R-Fc chimera (R&D Systems, 306-IR-050). Given that knockdown of DDX39B increases skipping of IL7R exon 6, the inventors expected secretion of sIL7R to increase in the knockdown. For this reason, the inventors used a one-sided Student's t-test to assess statistical significance, comparing each independent siRNA against the negative control (FIG. 1D). This experiment was performed twice with similar results.

RT-qPCR expression analyses. Transcript expression analyses in PBMCs and LCLs were carried out by RT-qPCR. The inventors used 0.2-0.7 µg of DNase-treated RNA as template for reverse transcription using the ImProm-II Reverse Transcription System (Promega) and oligo(dT) primers. cDNAs were diluted 1:5 and RT-qPCR reactions were carried out using Power SYBR Green PCR Master Mix (Applied Biosystems), with 5 µL of the corresponding cDNA, and 200 nM of the corresponding forward and reverse RT-qPCR primers. The relative abundance of the target genes (DDX39B, MICB, MCCD1, ATP6V1G2, NFKBIL1, LTA, TNF and LTB) was determined with gene-specific assays spanning an exon junction and normalized to GAPDH. The data were stratified by rs2523506 genotypes and normalized to rs2523506 CC genotype. Each point in the box plots represents measurements in PBMCs or LCLs from one individual and is shown as the average of technical triplicates. Statistical significance was established using the Student's t-test (two-sided).

Overall abundance of IL7R transcripts in rescue experiment and knockdown in primary CD4+ T cells was determined by RT-qPCR as before with primers complementary to the constitutively spliced exons 3 (forward) and 4 (reverse). IL7R levels were normalized to GAPDH, and the data is shown as fold-change over the negative control. Statistical significance was established using the Student's t-test (two-sided).

Global splicing analysis by RNA-seq. Global assessment of alternative splicing events regulated by DDX39B was carried out by DDX39B knockdown followed by RNA-seq. Knockdown was performed as before with DDX39B siRNAs DDX_3 and DDX_4, and control siRNA (NSC) in two independent experiments. Poly-A$^+$ RNA was enriched from 1 µg of total RNA and used as template to generate libraries using the Illumina TruSeq platform as recommended by the manufacturer. Libraries were sequenced on a 2×100 format on an Illumina Hi-Seq 1500. Splicing analysis was carried out using Vast-tools program version 0.2.1 (Irimia et al., 2014) by aligning the paired-end reads to the vast-tools human database (vastdb.hsa.7.3.14) using the default parameters. Two replicates of each condition were compared with the diff function of vast-tools to determine differential splicing. Two parameters were used to establish differential splicing events: E[ΔPsi], which refers to the difference in splicing between the experimental siRNAs (DDX_3 or DDX_4) and control siRNA (NSC) (positive and negative values indicate up-regulation and down-regulation, respectively), and max(x)@P(|ΔPsi|>x)>0.95, which indicates the change in splicing at 95% confidence level. To control for off-target effects, the inventors only considered changes in splicing with max(x)@P(|ΔPsi|>x)>0.95≥10.0 with at least one DDX39B siRNA but E[ΔPsi]≥+/−20.0 with both DDX39B siRNAs.

DDX39B western blot analyses in LCLs. Cell lysates were harvested from each cell line at two independent times using 1×RIPA buffer as before. Each cell lysate (10 µg of total protein per lane) was blotted twice, and the values presented correspond to the average of the independent measurements. To obtain more accurate measurements of relative protein abundance, DDX39B protein levels were normalized to either hnRNPA1 (FIG. 3C) or PTBP1 (not shown), yielding similar results. DDX39B and hnRNPA1 were blotted as before, whereas PTBP1 was blotted using custom-made anti-PTB rabbit serum (Wagner and Garcia-Blanco, 2002). The inventors used the Student's t-test (two-sided) to assess statistical significance of the findings.

Luciferase translation efficiency assays. Luciferase reporters were generated by cloning the different DDX39B 5' UTR variants into pcDNA5 plasmid containing the coding sequence of Renilla luciferase (R-Luc). DDX39B 5' UTR variants were synthesized as gBlocks (Integrated DNA Technologies) and cloned immediately upstream of the R-Luc ORF using HindIII (5') and KpnI (3') restriction sites. All constructs were verified by sequencing. DDX39B 5' UTR-R-Luc reporters (25 ng/well) were independently co-transfected with a Firefly luciferase control (F-Luc, 10 ng/well) into HeLa cells in 24-well format using Lipofectamine 2000 as indicated by the manufacturer. 24 hours post-transfection cell lysates were collected for luciferase assays with Passive Lysis Buffer and Luciferase assays were immediately performed using the Dual Luciferase Reporter Assay System (Promega). Total RNA was isolated from independent wells and converted into cDNA as above. RNA level for experimental and control reporters was quantified by RT-qPCR as before using primers complementary to the R-Luc and F-Luc ORFs, respectively. Luciferase activity and RNA levels were determined by normalizing R-Luc signals to F-Luc signals (R-Luc/F-Luc). Translational efficiency was then determined by dividing normalized Luciferase activity by normalized RNA levels. Statistical significance was assessed by Student's t-test (two-sided).

Genetic association and gene-gene interaction analyses. The inventors used genotypic data from six genetic cohorts of non-overlapping case and control subjects of European descent, imputed to >37.4 million SNPs across the genome using BEAGLE and 1000 Genomes Interim Phase I haplotypes using standard procedures (Patsopoulos et al., 2011). The inventors analyzed SNPs within 10 kilobases of autosomal candidate genes with ≥80% information and minor allele frequency >1% (4882 SNPs in 96 of the 116 candidate genes). EIGENSOFT, a principle components algorithm, identified genetic outliers and calculated the top 10 eigenvectors of the genotype data within each cohort; the first 5 eigenvectors sufficiently accounted for population stratification (Patsopoulos et al., 2011). Each variant was analyzed using a meta-analytic logistic regression model as implemented in PLINK (Purcell et al., 2007), assuming alleles have an additive effect on the log-odds scale within each cohort. Each model included the top 5 principal components. The inventors assumed the genetic effects were fixed across all cohorts, as previously performed for these data (Patsopoulos et al., 2013; Patsopoulos et al., 2011). One candidate gene (DDX39B) resides within the MHC, therefore meta-analyses for this locus were also adjusted for known HLA risk variants (HLA-adjusted model, included HLA-DRB1*15:01, HLA-DRB1*03:01, HLA-DRB1*13:01, HLA-DRB1*04:04, HLA-DRB1*04:01, HLA-DRB1*14:01, HLA-A*02:01, rs9277489, HLA-B*37:01, and HLA-B*38:01), and subsequently for an additional non-HLA MHC risk variant, rs2516489 (MHC-adjusted model). These risk variants within MHC region were imputed using BEAGLE (Browning and Browning, 2009; Patsopoulos et al., 2013) by leveraging a collection of 2,767 individuals of the Type 1 Diabetes Genetics Consortium with typed classical HLA alleles as previously described and validated (International et al., 2010; Patsopoulos et al., 2013; Raychaudhuri et al., 2012). The inventors used a logistic regression model in STATA (StataCorp) to investigate a multiplicative interaction between DDX39B rs2523506 and IL7R rs6897932, which was characterized further in IL7R rs6897932 and DDX39B rs2523506 stratified analyses. Similar methodology was employed to study interaction between HLA-DRB1*15:01 and IL7R rs6897932. The joint genotypic effect of rs2523506 and rs6897932 on MS risk was determined by comparing each genotypic combination to the reference (non-carriers of risk alleles at both loci). All models were adjusted for population stratification, cohort origin and HLA risk variants.

Molecular analyses. Statistical significance of all molecular analyses in this study was assessed by Student's t-test (two-sided; * p≤0.0005;  p≤0.005; * p≤0.05). Sample sizes for expression analyses in PBMCs and LCLs are indicated in the text and in the legend of the corresponding figures. Data on expression analyses in PBMCs and LCLs is shown as median with interquartile range, whereas data on knockdown and rescue experiments is presented as mean±s.d. These measurements are indicated in the legend of the corresponding figures.

Genetic Association Analyses and gene-gene interaction. Logistic regression models were used to examine the relationship between genetic variants and multiple sclerosis disease status (binary trait); the inventors report odds ratios and 95% confidence intervals in the text. Genome-wide statistical significance was imposed for these meta-analytic models (two-sided; p≤5×10−8). Models for variants residing within the MHC: having met the significance threshold, were subsequently adjusted for all other known MS MHC risk variants; statistical significance of p≤0.05 was imposed for these fully parameterized models. Similar significance threshold of p≤0.05 was imposed for the interactions between IL7R rs6897932 and DDX39B rs2523506, and HLA-DRB1*15:01 and IL7R rs6897932. Sample sizes for these analyses are reported in the text.

Data and Software Availability. The accession number for the RNA-seq dataset reported in this paper is GEO: GSE94730.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Allcock, R. J., Williams, J. H., and Price, P. (2001). The central MHC gene, BAT1, may encode a protein that down-regulates cytokine production. Genes Cells 6, 487-494.

Alves, N. L., van Leeuwen, E. M., Derks, I. A., and van Lier, R. A. (2008). Differential regulation of human IL-7 receptor alpha expression by IL-7 and TCR signaling. Journal of immunology 180, 5201-5210.

Anderson, C. A., Boucher, G., Lees, C. W., Franke, A., D'Amato, M., Taylor, K. D., Lee, J. C., Goyette, P., Imielinski, M., Latiano, A., et al. (2011). Meta-analysis identifies 29 additional ulcerative colitis risk loci, increasing the number of confirmed associations to 47. Nature genetics 43, 246-252.

Badot, V., Durez, P., Van den Eynde, B. J., Nzeusseu-Toukap, A., Houssiau, F. A., and Lauwerys, B. R. (2011). Rheumatoid arthritis synovial fibroblasts produce a soluble form of the interleukin-7 receptor in response to pro-inflammatory cytokines. J Cell Mol Med 15, 2335-2342.

Barrett, J. C., Clayton, D. G., Concannon, P., Akolkar, B., Cooper, J. D., Erlich, H. A., Julier, C., Morahan, G., Nerup, J., Nierras, C., et al. (2009). Genome-wide association study and meta-analysis find that over 40 loci affect risk of type 1 diabetes. Nature genetics 41, 703-707.

Bilal, M. Y., Vacaflores, A., and Houtman, J. C. (2015). Optimization of methods for the genetic modification of human T cells. Immunol Cell Biol 93, 896-908.

Briggs, F. B., Ramsay, P. P., Madden, E., Norris, J. M., Holers, V. M., Mikuls, T. R., Sokka, T., Seldin, M. F., Gregersen, P. K., Criswell, L. A., et al. (2010). Supervised machine learning and logistic regression identifies novel epistatic risk factors with PTPN22 for rheumatoid arthritis. Genes Immun 11, 199-208.

Browning, B. L., and Browning, S. R. (2009). A unified approach to genotype imputation and haplotype-phase inference for large data sets of trios and unrelated individuals. American journal of human genetics 84, 210-223.

Cheong, K. Y., Allcock, R. J., Eerligh, P., Witt, C. S., Christiansen, F. T., McCann, V., and Price, P. (2001). Localization of central MHC genes influencing type I diabetes. Human immunology 62, 1363-1370.

Crawley, A. M., Faucher, S., and Angel, J. B. (2010). Soluble IL-7R alpha (sCD127) inhibits IL-7 activity and is increased in HIV infection. Journal of immunology 184, 4679-4687.

de Bakker, P. I., McVean, G., Sabeti, P. C., Miretti, M. M., Green, T., Marchini, J., Ke, X., Monsuur, A. J., Whittaker, P., Delgado, M., et al. (2006). A high-resolution HLA and SNP haplotype map for disease association studies in the extended human MHC. Nature genetics 38, 1166-1172.

Degli-Esposti, M. A., Leelayuwat, C., and Dawkins, R. L. (1992). Ancestral haplotypes carry haplotypic and haplospecific polymorphisms of BAT1: possible relevance to autoimmune disease. Eur J Immunogenet 19, 121-127.

Dooms, H. (2013). Interleukin-7: Fuel for the autoimmune attack. Journal of autoimmunity 45, 40-48.

Evsyukova, I., Bradrick, S. S., Gregory, S. G., and Garcia-Blanco, M. A. (2013). Cleavage and polyadenylation specificity factor 1 (CPSF1) regulates alternative splicing of interleukin 7 receptor (IL7R) exon 6. Rna 19, 103-115.

Fleckner, J., Zhang, M., Valcarcel, J., and Green, M. R. (1997). U2AF65 recruits a novel human DEAD box protein required for the U2 snRNP-branchpoint interaction. Genes Dev 11, 1864-1872.

Fry, T. J., and Mackall, C. L. (2005). The many faces of IL-7: from lymphopoiesis to peripheral T cell maintenance. Journal of immunology 174, 6571-6576.

Gregory, S. G., Schmidt, S., Seth, P., Oksenberg, J. R., Hart, J., Prokop, A., Caillier, S. J., Ban, M., Goris, A., Barcellos, L. F., et al. (2007). Interleukin 7 receptor alpha chain (IL7R) shows allelic and functional association with multiple sclerosis. Nature genetics 39, 1083-1091.

Hoe, E., McKay, F. C., Schibeci, S. D., Gandhi, K., Heard, R. N., Stewart, G. J., and Booth, D. R. (2010). Functionally significant differences in expression of disease-associated IL-7 receptor alpha haplotypes in CD4 T cells and dendritic cells. Journal of immunology 184, 2512-2517.

Honig, A., Auboeuf, D., Parker, M. M., O'Malley, B. W., and Berget, S. M. (2002). Regulation of alternative splicing by the ATP-dependent DEAD-box RNA helicase p72. Mol Cell Biol 22, 5698-5707.

Huang, W., Thomas, B., Flynn, R. A., Gavzy, S. J., Wu, L., Kim, S. V., Hall, J. A., Miraldi, E. R., Ng, C. P., Rigo, F., et al. (2015). DDX5 and its associated lncRNA Rmrp modulate TH17 cell effector functions. Nature 528, 517-522.

International HapMap, C. (2003). The International HapMap Project. Nature 426, 789-796.

International HapMap, C. (2005). A haplotype map of the human genome. Nature 437, 1299-1320.

International HapMap, C., Frazer, K. A., Ballinger, D. G., Cox, D. R., Hinds, D. A., Stuve, L. L., Gibbs, R. A., Belmont, J. W., Boudreau, A., Hardenbol, P., et al. (2007). A second generation human haplotype map of over 3.1 million SNPs. Nature 449, 851-861.

International, H.I.V.C.S., Pereyra, F., Jia, X., McLaren, P. J., Telenti, A., de Bakker, P. I., Walker, B. D., Ripke, S., Brumme, C. J., Pulit, S. L., et al. (2010). The major genetic determinants of HIV-1 control affect HLA class I peptide presentation. Science 330, 1551-1557.

International Multiple Sclerosis Genetics, C., Hafler, D. A., Compston, A., Sawcer, S., Lander, E. S., Daly, M. J., De Jager, P. L., de Bakker, P. I., Gabriel, S. B., Mirel, D. B., et al. (2007). Risk alleles for multiple sclerosis identified by a genomewide study. N Engl J Med 357, 851-862.

International Multiple Sclerosis Genetics, C., International, I.B.D.G.C., and International, I.B.D.G.C.I. (2015). Class II HLA interactions modulate genetic risk for multiple sclerosis. Nature genetics.

Irimia, M., Weatheritt, R. J., Ellis, J. D., Parikshak, N. N., Gonatopoulos-Pournatzis, T., Babor, M., Quesnel-Vallieres, M., Tapial, J., Raj, B., O'Hanlon, D., et al. (2014). A highly conserved program of neuronal microexons is misregulated in autistic brains. Cell 159, 1511-1523.

Kaiser, C., Dobrikova, E. Y., Bradrick, S. S., Shveygert, M., Herbert, J. T., and Gromeier, M. (2008). Activation of cap-independent translation by variant eukaryotic initiation factor 4G in vivo. Rna 14, 2170-2182.

Kilding, R., Iles, M. M., Timms, J. M., Worthington, J., and Wilson, A. G. (2004). Additional genetic susceptibility for rheumatoid arthritis telomeric of the DRB1 locus. Arthritis and rheumatism 50, 763-769.

Lauwerys, B. R., Husson, S. N., Maudoux, A. L., Badot, V., and Houssiau, F. A. (2014). sIL7R concentrations in the serum reflect disease activity in the lupus kidney. Lupus Sci Med 1, e000036.

Lawson, B. R., Gonzalez-Quintial, R., Eleftheriadis, T., Farrar, M. A., Miller, S. D., Sauer, K., McGavern, D. B., Kono, D. H., Baccala, R., and Theofilopoulos, A. N. (2015). Interleukin-7 is required for CD4(+) T cell activation and autoimmune neuroinflammation. Clin Immunol 161, 260-269.

Lundmark, F., Duvefelt, K., Iacobaeus, E., Kockum, I., Wallstrom, E., Khademi, M., Oturai, A., Ryder, L. P., Saarela, J., Harbo, H. F., et al. (2007). Variation in interleukin 7 receptor alpha chain (IL7R) influences risk of multiple sclerosis. Nature genetics 39, 1108-1113.

Lundstrom, W., Highfill, S., Walsh, S. T., Beq, S., Morse, E., Kockum, I., Alfredsson, L., Olsson, T., Hillert, J., and Mackall, C. L. (2013). Soluble IL7Ralpha potentiates IL-7 bioactivity and promotes autoimmunity. Proceedings of the National Academy of Sciences of the United States of America 110, E1761-1770.

Luo, M. L., Zhou, Z., Magni, K., Christoforides, C., Rappsilber, J., Mann, M., and Reed, R. (2001). Pre-mRNA splicing and mRNA export linked by direct interactions between UAP56 and Aly. Nature 413, 644-647.

Maraskovsky, E., Teepe, M., Morrissey, P. J., Braddy, S., Miller, R. E., Lynch, D. H., and Peschon, J. J. (1996). Impaired survival and proliferation in IL-7 receptor-deficient peripheral T cells. Journal of immunology 157, 5315-5323.

Masuda, S., Das, R., Cheng, H., Hurt, E., Dorman, N., and Reed, R. (2005). Recruitment of the human TREX complex to mRNA during splicing. Genes Dev 19, 1512-1517.

Mazzucchelli, R., and Durum, S. K. (2007). Interleukin-7 receptor expression: intelligent design. Nat Rev Immunol 7, 144-154.

Monti, P., Brigatti, C., Krasmann, M., Ziegler, A. G., and Bonifacio, E. (2013). Concentration and activity of the soluble form of the interleukin-7 receptor alpha in type 1 diabetes identifies an interplay between hyperglycemia and immune function. Diabetes 62, 2500-2508.

Munitic, I., Williams, J. A., Yang, Y., Dong, B., Lucas, P. J., El Kassar, N., Gress, R. E., and Ashwell, J. D. (2004). Dynamic regulation of IL-7 receptor expression is required for normal thymopoiesis. Blood 104, 4165-4172.

Nakamura, M., Nishida, N., Kawashima, M., Aiba, Y., Tanaka, A., Yasunami, M., Nakamura, H., Komori, A., Nakamuta, M., Zeniya, M., et al. (2012). Genome-wide association study identifies TNFSF15 and POU2AF1 as susceptibility loci for primary biliary cirrhosis in the Japanese population. American journal of human genetics 91, 721-728.

Okamoto, K., Makino, S., Yoshikawa, Y., Takaki, A., Nagatsuka, Y., Ota, M., Tamiya, G., Kimura, A., Bahram, S., and Inoko, H. (2003). Identification of I kappa BL as the second major histocompatibility complex-linked susceptibility locus for rheumatoid arthritis. American journal of human genetics 72, 303-312.

Park, J. H., Yu, Q., Erman, B., Appelbaum, J. S., Montoya-Durango, D., Grimes, H. L., and Singer, A. (2004). Suppression of IL7Ralpha transcription by IL-7 and other prosurvival cytokines: a novel mechanism for maximizing IL-7-dependent T cell survival. Immunity 21, 289-302.

Paternoster, L., Standl, M., Chen, C. M., Ramasamy, A., Bonnelykke, K., Duijts, L., Ferreira, M. A., Alves, A. C., Thyssen, J. P., Albrecht, E., et al. (2012). Meta-analysis of genome-wide association studies identifies three new risk loci for atopic dermatitis. Nature genetics 44, 187-192.

Patsopoulos, N. A., Barcellos, L. F., Hintzen, R. Q., Schaefer, C., van Duijn, C. M., Noble, J. A., Raj, T., Imsgc, Anzgene, Gourraud, P. A., et al. (2013). Fine-mapping the genetic association of the major histocompatibility complex in multiple sclerosis: HLA and non-HLA effects. PLoS genetics 9, e1003926.

Patsopoulos, N. A., Bayer Pharma, M.S.G.W.G., Steering Committees of Studies Evaluating, I.-b., a, C.C.R.A., Consortium, A.N., GeneMsa, International Multiple Sclerosis Genetics, C., Esposito, F., Reischl, J., Lehr, S., et al. (2011). Genome-wide meta-analysis identifies novel multiple sclerosis susceptibility loci. Annals of neurology 70, 897-912.

Perdigones, N., Vigo, A. G., Lamas, J. R., Martinez, A., Balsa, A., Pascual-Salcedo, D., de la Concha, E. G., Fernandez-Gutierrez, B., and Urcelay, E. (2010). Evidence of epistasis between TNFRSF14 and TNFRSF6B polymorphisms in patients with rheumatoid arthritis. Arthritis and rheumatism 62, 705-710.

Peschon, J. J., Morrissey, P. J., Grabstein, K. H., Ramsdell, F. J., Maraskovsky, E., Gliniak, B. C., Park, L. S., Ziegler, S. F., Williams, D. E., Ware, C. B., et al. (1994). Early lymphocyte expansion is severely impaired in interleukin 7 receptor-deficient mice. J Exp Med 180, 1955-1960.

Price, P., Wong, A. M., Williamson, D., Voon, D., Baltic, S., Allcock, R. J., Boodhoo, A., and Christiansen, F. T. (2004). Polymorphisms at positions -22 and -348 in the promoter of the BAT1 gene affect transcription and the binding of nuclear factors. Human molecular genetics 13, 967-974.

Puel, A., Ziegler, S. F., Buckley, R. H., and Leonard, W. J. (1998). Defective IL7R expression in T(-)B(+)NK(+) severe combined immunodeficiency. Nature genetics 20, 394-397.

Purcell, S., Neale, B., Todd-Brown, K., Thomas, L., Ferreira, M. A., Bender, D., Maller, J., Sklar, P., de Bakker, P. I., Daly, M. J., et al. (2007). PLINK: a tool set for whole-genome association and population-based linkage analyses. American journal of human genetics 81, 559-575.

Quinones-Lombrana, A., Lopez-Soto, A., Ballina-Garcia, F. J., Alpert-Lopez, M., Queiro-Silva, R., Lopez-Vazquez, A., Lopez-Larrea, C., and Gonzalez, S. (2008). BAT1 promoter polymorphism is associated with rheumatoid arthritis susceptibility. J Rheumatol 35, 741-744.

Raychaudhuri, S., Sandor, C., Stahl, E. A., Freudenberg, J., Lee, H. S., Jia, X., Alfredsson, L., Padyukov, L., Klareskog, L., Worthington, J., et al. (2012). Five amino acids in three HLA proteins explain most of the association between MHC and seropositive rheumatoid arthritis. Nature genetics 44, 291-296.

Roifman, C. M., Zhang, J., Chitayat, D., and Sharfe, N. (2000). A partial deficiency of interleukin-7R alpha is sufficient to abrogate T-cell development and cause severe combined immunodeficiency. Blood 96, 2803-2807.

Shahbazi, M., Roshandel, D., Omidnyia, E., and Rshaidbaghan, A. (2011). Interaction of HLA-DRB1*1501 allele and TNF-alpha -308 G/A single nucleotide polymorphism in the susceptibility to multiple sclerosis. Clin Immunol 139, 277-281.

Shen, H., Zheng, X., Shen, J., Zhang, L., Zhao, R., and Green, M. R. (2008). Distinct activities of the DExD/H-box splicing factor hUAP56 facilitate stepwise assembly of the spliceosome. Genes Dev 22, 1796-1803.

Shen, J., Zhang, L., and Zhao, R. (2007). Biochemical characterization of the ATPase and helicase activity of UAP56, an essential pre-mRNA splicing and mRNA export factor. J Biol Chem 282, 22544-22550.

Sospedra, M., and Martin, R. (2005). Immunology of multiple sclerosis. Annual review of immunology 23, 683-747.

Strasser, K., Masuda, S., Mason, P., Pfannstiel, J., Oppizzi, M., Rodriguez-Navarro, S., Rondon, A. G., Aguilera, A., Struhl, K., Reed, R., et al. (2002). TREX is a conserved complex coupling transcription with messenger RNA export. Nature 417, 304-308.

Teigelkamp, S., Mundt, C., Achsel, T., Will, C. L., and Luhrmann, R. (1997). The human U5 snRNP-specific 100-kD protein is an RS domain-containing, putative RNA helicase with significant homology to the yeast splicing factor Prp28p. Rna 3, 1313-1326.

Todd, J. A., Walker, N. M., Cooper, J. D., Smyth, D. J., Downes, K., Plagnol, V., Bailey, R., Nejentsev, S., Field, S. F., Payne, F., et al. (2007). Robust associations of four new chromosome regions from genome-wide analyses of type 1 diabetes. Nature genetics 39, 857-864.

Wagner, E. J., and Garcia-Blanco, M. A. (2002). RNAi-mediated PTB depletion leads to enhanced exon definition. Mol Cell 10, 943-949.

Wong, A. M., Allcock, R. J., Cheong, K. Y., Christiansen, F. T., and Price, P. (2003). Alleles of the proximal promoter of BAT1, a putative anti-inflammatory gene adjacent to the TNF cluster, reduce transcription on a disease-associated MHC haplotype. Genes Cells 8, 403-412.

Wu, L., Candille, S. I., Choi, Y., Xie, D., Jiang, L., Li-Pook-Than, J., Tang, H., and Snyder, M. (2013). Variation and genetic control of protein abundance in humans. Nature 499, 79-82.

Yuan, Y., Tian, L., Lu, D., and Xu, S. (2015). Analysis of genome-wide RNA-sequencing data suggests age of the CEPH/Utah (CEU) lymphoblastoid cell lines systematically biases gene expression profiles. Sci Rep 5, 7960.

Zhou, X. J., Lu, X. L., Nath, S. K., Lv, J. C., Zhu, S. N., Yang, H. Z., Qin, L. X., Zhao, M. H., Su, Y., Shen, N., et al. (2012). Gene-gene interaction of BLK, TNFSF4, TRAF1, TNFAIP3, and REL in systemic lupus erythematosus. Arthritis and rheumatism 64, 222-231.

What is claimed is:

1. A method of selecting for treatment a subject with an autoimmune disease caused by lower levels of an RNA Helicase DDX39B, comprising:

obtaining a biological sample from a subject suspected of having an autoimmune disease;

detecting or measuring in the biological sample an amount of an RNA Helicase DDX39B, wherein a patient is elected for treatment if they have a lower expression or activity of the RNA Helicase DDX39B;

detecting or measuring in the biological sample an amount of the soluble interleukin-7 receptor (SiL7R); and selecting a treatment for the subject that has increased levels of soluble interleukin-7 receptor (SiL7R) when compared to a sample from a human subject not having an autoimmune disease and decreased expression or activity of RNA Helicase DDX39B.

2. The method of claim 1, further comprising selecting a treatment selected from mitoxatrone, interferon beta-1a, PEG-interferon beta-1a, azathioprine, fingolimod, natalizumab, or methylprednisone.

* * * * *

SEQUENCE LISTING

```
<160> NUMBER OF SEQ ID NOS: 35

<210> SEQ ID NO 1
<211> LENGTH: 39
<212> TYPE: DNA
<213> ORGANISM: Artificial Sequence
<220> FEATURE:
<223> OTHER INFORMATION: Synthetic primer

<400> SEQUENCE: 1
aagcttgcca ccatggcaga gaacgatgtg gacaatgag                          39

<210> SEQ ID NO 2
<211> LENGTH: 33
<212> TYPE: DNA
<213> ORGANISM: Artificial Sequence
<220> FEATURE:
<223> OTHER INFORMATION: Synthetic primer

<400> SEQUENCE: 2
ctcgagctac cgtgtctgtt caatgtagga gga                                33

<210> SEQ ID NO 3
<211> LENGTH: 23
<212> TYPE: DNA
<213> ORGANISM: Artificial Sequence
<220> FEATURE:
<223> OTHER INFORMATION: Synthetic primer

<400> SEQUENCE: 3
taatacgact cactatenggg aga                                          23

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
atttaggtga cactatagaa                                               20

<210> SEQ ID NO 5
<211> LENGTH: 27
<212> TYPE: DNA
<213> ORGANISM: Artificial Sequence
<220> FEATURE:
<223> OTHER INFORMATION: Synthetic primer

<400> SEQUENCE: 5
ggcagcaatg tatgagatta aagttcg                                       27

<210> SEQ ID NO 6
<211> LENGTH: 29
<212> TYPE: DNA
<213> ORGANISM: Artificial Sequence
<220> FEATURE:
<223> OTHER INFORMATION: Synthetic primer

<400> SEQUENCE: 6
caaagatgtt ccagagtctt cttatgatc                                     29

<210> SEQ ID NO 7
<211> LENGTH: 25
<212> TYPE: DNA
<213> ORGANISM: Artificial Sequence
```

<220> FEATURE:
<223> OTHER INFORMATION: Synthetic primer

<400> SEQUENCE: 7
caatatatgt gtgaaggttg gagaa                                    25

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
cattggctcc ttcccgatag                                          20

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
agccacatcg ctcagacac                                           19

<210> SEQ ID NO 10
<211> LENGTH: 19
<212> TYPE: DNA
<213> ORGANISM: Artificial Sequence
<220> FEATURE:
<223> OTHER INFORMATION: Synthetic primer

<400> SEQUENCE: 10
gcccaatacg accaaatcc                                           19

<210> SEQ ID NO 11
<211> LENGTH: 21
<212> TYPE: DNA
<213> ORGANISM: Artificial Sequence
<220> FEATURE:
<223> OTHER INFORMATION: Synthetic primer

<400> SEQUENCE: 11
gtgctacctt gagcaaagag a                                        21

<210> SEQ ID NO 12
<211> LENGTH: 17
<212> TYPE: DNA
<213> ORGANISM: Artificial Sequence
<220> FEATURE:
<223> OTHER INFORMATION: Synthetic primer

<400> SEQUENCE: 12
aacccatgca gcgtcaa                                             17

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
agcaagtgag cgaccttatc                                          20

```
<210> SEQ ID NO 14
<211> LENGTH: 21
<212> TYPE: DNA
<213> ORGANISM: Artificial Sequence
<220> FEATURE:
<223> OTHER INFORMATION: Synthetic primer

<400> SEQUENCE: 14
catccttcat gcctcctcta c                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
aggccaatca ggctatcaat c                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
ctgaagaagt ggtccggtaa c                                              21

<210> SEQ ID NO 17
<211> LENGTH: 23
<212> TYPE: DNA
<213> ORGANISM: Artificial Sequence
<220> FEATURE:
<223> OTHER INFORMATION: Synthetic primer

<400> SEQUENCE: 17
tccaagatgt gtctatggtt gtc                                            23

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
gaacacagca gagtcctctt t                                              21

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
atggaacaca gcgggaat                                                  18

<210> SEQ ID NO 20
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 20
catggcatag cagcagaaac                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
caaagcaagc atggaagagc                                              20

<210> SEQ ID NO 22
<211> LENGTH: 19
<212> TYPE: DNA
<213> ORGANISM: Artificial Sequence
<220> FEATURE:
<223> OTHER INFORMATION: Synthetic primer

<400> SEQUENCE: 22
ctgctgctcc aacaactct                                               19

<210> SEQ ID NO 23
<211> LENGTH: 19
<212> TYPE: DNA
<213> ORGANISM: Artificial Sequence
<220> FEATURE:
<223> OTHER INFORMATION: Synthetic primer

<400> SEQUENCE: 23
agcttcttgg catggtctg                                               19

<210> SEQ ID NO 24
<211> LENGTH: 22
<212> TYPE: DNA
<213> ORGANISM: Artificial Sequence
<220> FEATURE:
<223> OTHER INFORMATION: Synthetic primer

<400> SEQUENCE: 24
gatttctttg agggagggaa ct                                           22

<210> SEQ ID NO 25
<211> LENGTH: 17
<212> TYPE: DNA
<213> ORGANISM: Artificial Sequence
<220> FEATURE:
<223> OTHER INFORMATION: Synthetic primer

<400> SEQUENCE: 25
gggacacggc actgcat                                                 17

<210> SEQ ID NO 26
<211> LENGTH: 17
<212> TYPE: DNA
<213> ORGANISM: Artificial Sequence
<220> FEATURE:
<223> OTHER INFORMATION: Synthetic primer

<400> SEQUENCE: 26
ggagggacag cggctta                                                 17

<210> SEQ ID NO 27
```

```
<211> LENGTH: 18
<212> TYPE: DNA
<213> ORGANISM: Artificial Sequence
<220> FEATURE:
<223> OTHER INFORMATION: Synthetic primer

<400> SEQUENCE: 27
caaacctgct gctcacct                                                    18

<210> SEQ ID NO 28
<211> LENGTH: 19
<212> TYPE: DNA
<213> ORGANISM: Artificial Sequence
<220> FEATURE:
<223> OTHER INFORMATION: Synthetic primer

<400> SEQUENCE: 28
ggaaccagga gaattgttg                                                   19

<210> SEQ ID NO 29
<211> LENGTH: 19
<212> TYPE: DNA
<213> ORGANISM: Artificial Sequence
<220> FEATURE:
<223> OTHER INFORMATION: Synthetic primer

<400> SEQUENCE: 29
caagcctgta gcccatgtt                                                   19

<210> SEQ ID NO 30
<211> LENGTH: 21
<212> TYPE: DNA
<213> ORGANISM: Artificial Sequence
<220> FEATURE:
<223> OTHER INFORMATION: Synthetic primer

<400> SEQUENCE: 30
ggagccagaa acagatctca g                                                21

<210> SEQ ID NO 31
<211> LENGTH: 17
<212> TYPE: DNA
<213> ORGANISM: Artificial Sequence
<220> FEATURE:
<223> OTHER INFORMATION: Synthetic primer

<400> SEQUENCE: 31
ctcgtcagaa acgcctg                                                     17

<210> SEQ ID NO 32
<211> LENGTH: 24
<212> TYPE: DNA
<213> ORGANISM: Artificial Sequence
<220> FEATURE:
<223> OTHER INFORMATION: Synthetic primer

<400> SEQUENCE: 32
cagtggtggg ccagatgtaa acaa                                             24

<210> SEQ ID NO 33
<211> LENGTH: 24
<212> TYPE: DNA
<213> ORGANISM: Artificial Sequence
<220> FEATURE:
<223> OTHER INFORMATION: Synthetic primer

<400> SEQUENCE: 33
```

```
taagaagagg ccgcgttacc atgt                                              24

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
cggaaagacg atgacggaaa                                                   20

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
cggtacttcg tccacaaaca                                                   20
```